United States Patent
Akitomi et al.

(10) Patent No.: US 9,797,888 B2
(45) Date of Patent: Oct. 24, 2017

(54) NUCLEIC ACID ELEMENT CANDIDATE MOLECULE AND SCREENING METHOD FOR SCREENING FOR NUCLEIC ACID ELEMENT FOR TARGET ANALYSIS USING THE SAME

(71) Applicant: NEC Solution Innovators, Ltd., Tokyo (JP)

(72) Inventors: Jou Akitomi, Tokyo (JP); Naoto Kaneko, Tokyo (JP); Katsunori Horii, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 0 days.

(21) Appl. No.: 14/770,520

(22) PCT Filed: Feb. 17, 2014

(86) PCT No.: PCT/JP2014/053664
§ 371 (c)(1),
(2) Date: Aug. 26, 2015

(87) PCT Pub. No.: WO2014/136560
PCT Pub. Date: Sep. 12, 2014

(65) Prior Publication Data
US 2016/0003811 A1 Jan. 7, 2016

(30) Foreign Application Priority Data
Mar. 8, 2013 (JP) .................. 2013-047341

(51) Int. Cl.
*G01N 33/53* (2006.01)
*C12Q 1/68* (2006.01)

(52) U.S. Cl.
CPC ....... *G01N 33/5308* (2013.01); *C12Q 1/6816* (2013.01)

(58) Field of Classification Search
None
See application file for complete search history.

(56) References Cited

U.S. PATENT DOCUMENTS

| 5,424,186 A | 6/1995 | Fodor et al. |
| 5,807,522 A | 9/1998 | Brown et al. |
| 2012/0202195 A1 | 8/2012 | Waga et al. |
| 2014/0128589 A1 | 5/2014 | Kaneko et al. |

FOREIGN PATENT DOCUMENTS

| EP | 2 463 660 A1 | 6/2012 |
| JP | H10-503841 A | 4/1998 |
| WO | WO-95-35505 A1 | 12/1995 |
| WO | WO-2011/016565 A1 | 2/2011 |
| WO | WO-2013/005723 A1 | 1/2013 |

OTHER PUBLICATIONS

Elbaz, et al. (2009) "Cooperative Multicomponent Self-Assembly of Nucleic Acid Structures for the Activation of DNAzyme Cascades: A Paradigm for DNA Sensors and Aptasensors", Chemistry: A European Journal, 15(4): 3411-18.*
International Search Report corresponding to PCT/JP2014/053664, dated Mar. 18, 2014 (6 pages).
Travascio et al., "DNA-enhanced Peroxidase Activity of a DNA Aptamer—Hemin Complex," Chemistry & Biology, vol. 5, Aug. 25, 1998, pp. 505-517.
Teller et al., "Aptamer—DNAzyme Hairpins for Amplified Biosensing," Analytical Chemistry, vol. 81, No. 21, Nov. 1, 2009, pp. 9114-9119.
Tao et al., "Label-Free Colorimetric Detection of Aqueous Mercury Ion (Hg2+) Using Hg2+-Modulated G-Quadruplex-Based DNAzymes," Analytical Chemistry, vol. 81, Mar. 15, 2009, pp. 2144-2149.
Li et al., "Amplified Analysis of Low-Molecular-Weight Substrates or Proteins by the Self-Assembly of DNAzyme-Aptamer Conjugates," Journal of the American Chemical Society, vol. 129, (2007), pp. 5804-5805.
Cheng et al., "General Peroxidase Activity of G-Quadruplex—Hemi Complexes and Its Application in Ligand Screening," Biochemistry, vol. 48, Jul. 20, 2009, pp. 7817-7823.

* cited by examiner

*Primary Examiner* — Robert M Kelly
(74) *Attorney, Agent, or Firm* — Wilmer Cutler Pickering Hale and Dorr LLP

(57) ABSTRACT

The present invention provides a novel nucleic acid element candidate molecule for use in screening for a nucleic acid element for target analysis and a novel screening method for screening for a nucleic acid element for target analysis using the same. The candidate molecule according to the present invention is a molecule for screening for a nucleic acid element for target analysis, being the following single-stranded nucleic acid (I): (I) a single-stranded nucleic acid comprising a catalyst sequence (D), a blocking sequence (B), and a binding sequence (A) that binds to a target, linked in this order. The blocking sequence (B) is complementary to a partial region (Dp) in the catalyst sequence (D). A terminal region (Ab) on the blocking sequence (B) side in the binding sequence (A) is complementary to a flanking region (Df) of the partial region (Dp) in the catalyst sequence (D) and is complementary to a terminal region (Af) on the side opposite to the blocking sequence (B) side in the binding sequence (A).

16 Claims, 7 Drawing Sheets

(A)

(B)  (C)

Blocking type    Activity type (A)

(B)  (C)

Blocking type    Activity type

| SEQ ID NO: | Name | Sequence | S/N ratio |
|---|---|---|---|
| 1 | N2_Mel06_P02_A1_D7TC | GGGTGGGAGGGGCGGgctcccacCGCTTTTTTTTTTGCGg | 1.53 |
| 2 | N2_Mel06_P05_A1_D4TC | GGGTGGGAGGGGCGGgctccCGCTTTTTTTTTTGCGg | 1.47 |
| 3 | N2_Mel13_P03_A2_D6TC | GGGTGGGAGGGGCGGgctcccaCGCTTTTTTTTTTGCGgtg | 1.47 |
| 4 | N2_Mel06_P06_A2_D5TC | GGGTGGGAGGGGCGGgccctcCGCTTTTTTTTTTGCG | 1.47 |
| 5 | N2_Mel13_P03_A0_D6TC | GGGTGGGAGGGGCGGgctccaCCGCTTTTTTTTTTCGG | 1.45 |
| 6 | N2_Mel13_P05_A1_D4TC | GGGTGGGAGGGGCGGgctcccCGTTTTTTTTTTCGG | 1.43 |
| 7 | N2_Mel06_P03_A2_D6TC | GGGTGGGAGGGGCGGgctcccaCGCTTTTTTTTTTGCGtg | 1.42 |
| 8 | N2_Mel06_P01_A1_D5TC | GGGTGGGAGGGGCGGgccaccCGCTTTTTTTTTTGCGg | 1.42 |
| 9 | N2_Mel06_P05_A1_D7TC | GGGTGGGAGGGGCGGgctccCGCTTTTTTTTTTGCGg | 1.42 |
| 10 | N2_Mel06_P03_A1_D7TC | GGGTGGGAGGGGCGGgctcccaCGCTTTTTTTTTTGCGt | 1.41 |
| 11 | N2_Mel06_P03_A0_D6TC | GGGTGGGAGGGGCGGgctcccaCGCTTTTTTTTTTGCG | 1.41 |
| 12 | N2_Mel06_P05_A0_D4TC | GGGTGGGAGGGGCGGgctccCGCTTTTTTTTTTGCG | 1.41 |
| 13 | N2_Mel06_P06_A1_D5TC | GGGTGGGAGGGGCGGgcctcCGCTTTTTTTTTTGCG | 1.40 |
| 14 | N2_Mel06_P06_A2_D4TC | GGGTGGGAGGGGCGGgcctcCGCTTTTTTTTTTGCGga | 1.40 |
| 15 | N2_Mel06_P06_A1_D3TC | GGGTGGGAGGGGCGGgcctcCGCTTTTTTTTTTGCGg | 1.40 |
| 16 | N2_Mel06_P02_A1_D5TC | GGGTGGGAGGGGCGGgccacCGCTTTTTTTTTTGCGg | 1.40 |
| 17 | N2_Mel06_P05_A2_D5TC | GGGTGGGAGGGGCGGgcctccCGCTTTTTTTTTTGCGg | 1.40 |
| 18 | N2_Mel06_P06_A2_D6TC | GGGTGGGAGGGGCGGgccctcCGCTTTTTTTTTTGCGga | 1.40 |

FIG. 3

| | | | |
|---|---|---|---|
| 19 | N2_Mel06_P06_A0_D4TC | GGGTGGGAGGGGCGGGcctcCGCTTTTTTTTTTGCG | 1.40 |
| 20 | N2_Mel06_P02_A1_D6TC | GGGTGGGAGGGGCGGGtcccacCGCTTTTTTTTTTGCGg | 1.39 |
| 21 | N2_Mel13_P06_A0_D3TC | GGGTGGGAGGGGCGGGcctcCCGTTTTTTTTTTCGG | 1.39 |
| 22 | N2_Mel13_P06_A2_D4TC | GGGTGGGAGGGGCGGGcctcCCGTTTTTTTTTTCGGga | 1.38 |
| 23 | N2_Mel13_P05_A2_D5TC | GGGTGGGAGGGGCGGGcctcCCGTTTTTTTTTTCGGgg | 1.38 |
| 24 | N2_Mel06_P06_A0_D4TC | GGGTGGGAGGGGCGGGcctcCCGTTTTTTTTTTCGG | 1.38 |
| 25 | N2_Mel06_P06_A1_D4TC | GGGTGGGAGGGGCGGGcctcCGCTTTTTTTTTTGCGg | 1.38 |
| 26 | N2_Mel06_P05_A2_D4TC | GGGTGGGAGGGGCGGGcctccCGCTTTTTTTTTTCGGgg | 1.38 |
| 27 | N2_Mel06_P03_A2_D7TC | GGGTGGGAGGGGCGGGcctcccaCGCTTTTTTTTTTGCGtg | 1.38 |
| 28 | N2_Mel06_P06_A1_D6TC | GGGTGGGAGGGGCGGGccctcCGCTTTTTTTTTTGCGg | 1.37 |
| 29 | N2_Mel13_P05_A0_D5TC | GGGTGGGAGGGGCGGGcctccCGCTTTTTTTTTTCGG | 1.36 |
| 30 | N2_Mel13_P05_A1_D4TC | GGGTGGGAGGGGCGGGcctccCGCTTTTTTTTTTCGGg | 1.36 |
| 31 | N2_Mel13_P07_A0_D2TC | GGGTGGGAGGGGCGGGcttCCGTTTTTTTTTTCGG | 1.36 |
| 32 | N2_Mel06_P01_A2_D4TC | GGGTGGGAGGGGCGGGccaccCgGCCTCGCTTTTTTTTTTGCGgg | 1.36 |
| 33 | N2_Mel06_P06_A0_D3TC | GGGTGGGAGGGGCGGGcctcCGCTTTTTTTTTTGCG | 1.36 |
| 34 | N2_Mel06_P07_A2_D4TC | GGGTGGGAGGGGCGGGcctCGCTTTTTTTTTTGCGag | 1.36 |
| 35 | N2_Mel13_P02_A2_D4TC | GGGTGGGAGGGGCGGGccaCCGCTTTTTTTTTTCGGgtt | 1.36 |
| 36 | N2_Mel06_P05_A1_D6TC | GGGTGGGAGGGGCGGGccctccCGCTTTTTTTTTTGCGg | 1.36 |

FIG. 3 (con't)

| 37 | N2_Mel06_P02_A2_D6TC | GGGTGGGAGGGGCGGGtccacCGCTTTTTTTTTGCGgt | 1.35 |
| 38 | N2_Mel06_P06_A2_D3TC | GGGTGGGAGGGGCGGgctccCGCTTTTTTTTTTGCGga | 1.35 |
| 39 | N2_Mel13_P05_A1_D5TC | GGGTGGGAGGGGCGGgctccCGCTTTTTTTTTTCGGg | 1.35 |
| 40 | N2_Mel13_P03_A2_D5TC | GGGTGGGAGGGGCGGGtccaCCGTTTTTTTTTCGGtg | 1.35 |
| 41 | N2_Mel06_P06_A1_D7TC | GGGTGGGAGGGGCGGgccctcCGCTTTTTTTTTGCGg | 1.35 |
| 42 | N2_Mel06_P01_A1_D6TC | GGGTGGGAGGGGCGGgccactcCGCTTTTTTTTTCGGg | 1.35 |
| 43 | N2_Mel13_P05_A1_D6TC | GGGTGGGAGGGGCGGgccctcCGCTTTTTTTTTCGGg | 1.35 |
| 44 | N1_Mel14_P11_A1_D5TC | GGGTGGGAGGGTCGGGccgaCCCTTTTTTTTTGCGt | 1.34 |
| 45 | N2_Mel06_P01_A1_D7TC | GGGTGGGAGGGGCGGtccacCGCTTTTTTTTTGCGg | 1.34 |
| 46 | N2_Mel06_P05_A0_D5TC | GGGTGGGAGGGGCGGgctccCGCTTTTTTTTTGCG | 1.33 |
| 47 | N2_Mel06_P06_A2_D7TC | GGGTGGGAGGGGCGGgccctcCGCTTTTTTTTTGCGga | 1.33 |
| 48 | N2_Mel06_P02_A0_D7TC | GGGTGGGAGGGGCGGgctccacCGCTTTTTTTTTGCG | 1.33 |
| 49 | N2_Mel06_P05_A1_D7TC | GGGTGGGAGGGGCGGgccctccCGCTTTTTTTTTGCGg | 1.33 |
| 50 | N2_Mel13_P06_A1_D4TC | GGGTGGGAGGGGCGGgcctcCGCTTTTTTTTTCGGg | 1.33 |
| 51 | N2_Mel13_P03_A2_D4TC | GGGTGGGAGGGGCGGgcccaCCGTTTTTTTTTCGGtg | 1.33 |
| 52 | N2_Mel13_P07_A1_D5TC | GGGTGGGAGGGGCGGgccctCCGTTTTTTTTTCGGa | 1.33 |
| 53 | N2_Mel13_P02_A2_D6TC | GGGTGGGAGGGGCGGgtccacCGTTTTTTTTTCGGgt | 1.33 |
| 54 | N2_Mel13_P07_A1_D2TC | GGGTGGGAGGGGCGGgctCCGTTTTTTTTTCGGa | 1.33 |

FIG. 3 (con't)

| SEQ ID NO: | Name | Sequence | S/N ratio |
|---|---|---|---|
| 55 | N2_Mel06_P07_A1_D4TC | GGGTGGGAGGGGCGGGccctCGTTTTTTTTTTGCGa | 1.33 |
| 56 | N2_Mel06_P02_A2_D4TC | GGGTGGGAGGGGCGGGccacCGCTTTTTTTTTTGCGgt | 1.33 |
| 57 | N2_Mel13_P07_A2_D5TC | GGGTGGGAGGGGCGGGccccctCGTTTTTTTTTTGCGag | 1.33 |
| 58 | N2_Mel06_P07_A2_D5TC | GGGTGGGAGGGGCGGGccccctCGTTTTTTTTTTGCGag | 1.32 |
| 59 | N2_Mel06_P01_A2_D6TC | GGGTGGGAGGGGCGGGcccacCGTTTTTTTTTTGCGgg | 1.32 |
| 60 | N2_Mel13_P06_A1_D3TC | GGGTGGGAGGGGCGGGctccCGTTTTTTTTTTCGGg | 1.32 |
| 61 | N2_Mel13_P07_A2_D6TC | GGGTGGGAGGGGCCGGGgccctCGTTTTTTTTTTCGGag | 1.32 |
| 62 | N2_Mel06_P07_A1_D5TC | GGGTGGGAGGGGCGGGccactcCGTTTTTTTTTTGCGa | 1.32 |
| 63 | N2_Mel13_P05_A0_D6TC | GGGTGGGAGGGGCGGGccctccCGTTTTTTTTTTCGGg | 1.32 |
| 64 | N2_Mel13_P02_A1_D4TC | GGGTGGGAGGGGCGGGccaccCGTTTTTTTTTTCGGg | 1.32 |
| 65 | N1_Mel13_P10_A2_D6TC | GGGTGGGAGGGGTCGGGcccgaccCGTTTTTTTTTTCGGgt | 1.32 |
| 66 | N2_Mel06_P03_A0_D4TC | GGGTGGGAGGGGCGGGcccaCGTTTTTTTTTTGCG | 1.32 |
| 67 | N2_Mel13_P07_A2_D4TC | GGGTGGGAGGGGCGGGccctCGTTTTTTTTTTCGGag | 1.32 |
| 68 | N2_Mel06_P06_A0_D6TC | GGGTGGGAGGGGCGGGccctcCGTTTTTTTTTTCGG | 1.32 |
| 69 | N2_Mel06_P07_A1_D3TC | GGGTGGGAGGGGCGGGccctCGTTTTTTTTTTCGGa | 1.32 |
| 70 | N2_Mel13_P07_A0_D4TC | GGGTGGGAGGGGCGGGccactCGTTTTTTTTTTCGG | 1.32 |
| 71 | N2_Mel13_P02_A0_D4TC | GGGTGGGAGGGGCGGGccactCGTTTTTTTTTTCGG | 1.31 |
| 72 | N2_Mel06_P06_A0_D5TC | GGGTGGGAGGGGCGGGccctcCGTTTTTTTTTTGCG | 1.31 |

FIG. 4

| | Name | Sequence | Score |
|---|---|---|---|
| 73 | N2_Mel06_P07_A0_D5TC | GGGTGGGAGGGGCGGGgccctCGCTTTTTTTTTTTTGCG | 1.31 |
| 74 | N2_Mel06_P01_A2_D7TC | GGGTGGGAGGGGCGGGgtccaccCgCTTTTTTTTTTTTGCGgg | 1.31 |
| 75 | N2_Mel13_P02_A1_D4TC | GGGTGGGAGGGGCGGGgccaccCgCTTTTTTTTTTTTGCGg | 1.31 |
| 76 | N2_Mel13_P01_A2_D5TC | GGGTGGGAGGGGCGGGgccaccCCGTTTTTTTTTTTTCGGgg | 1.31 |
| 77 | N2_Mel06_P03_A2_D5TC | GGGTGGGAGGGGCGGGgtcccaCgCTTTTTTTTTTTTGCgg | 1.31 |
| 78 | N2_Mel13_P06_A2_D3TC | GGGTGGGAGGGGCGGGgctcaCgCTTTTTTTTTTTTGCtg | 1.31 |
| 79 | N2_Mel13_P03_A0_D4TC | GGGTGGGAGGGGCGGGgcccaCgCTTTTTTTTTTTTCGga | 1.31 |
| 80 | N2_Mel06_P11_A1_D4TC | GGGTGGGAGGGGCGGGgccgacCgCTTTTTTTTTTTTGCgg | 1.31 |
| 81 | N2_Mel06_P06_A0_D6TC | GGGTGGGAGGGGCGGGgccctcCgCTTTTTTTTTTTTGCg | 1.31 |
| 82 | N1_Mel06_P10_A0_D6TC | GGGTGGGAGGGTCGGGgcccgacCGCTTTTTTTTTTTTCGG | 1.31 |
| 83 | N2_Mel06_P07_A0_D4TC | GGGTGGGAGGGGCGGGgctccCGCTTTTTTTTTTTTGCG | 1.31 |
| 84 | N2_Mel13_P05_A2_D4TC | GGGTGGGAGGGGCGGGgccaccCGCTTTTTTTTTTTTCGGgg | 1.31 |
| 85 | N2_Mel13_P01_A1_D5TC | GGGTGGGAGGGTCGGGgccaccCCGTTTTTTTTTTTTCGGg | 1.31 |
| 86 | N1_Mel14_P09_A1_D7TC | GGGTGGGAGGGTCGGGgcccgaccCgCTTTTTTTTTTTTGCGg | 1.31 |
| 87 | N2_Mel06_P07_A1_D7TC | GGGTGGGAGGGGCGGGgcgcccctgCCTTTTTTTTTTTTGCGa | 1.31 |
| 88 | N2_Mel13_P03_A2_D4TC | GGGTGGGAGGGGCGGGgccccagCGCTTTTTTTTTTTTGGG | 1.30 |
| 89 | N2_Mel06_P03_A2_D5TC | GGGTGGGAGGGGCGGGgccccgaCCGTTTTTTTTTTTTGCGtg | 1.30 |
| 90 | N2_Mel13_P07_A0_D5TC | GGGTGGGAGGGGCGGGgccctCCGTTTTTTTTTTTTCGG | 1.30 |

FIG. 4 (con't)

| | | | |
|---|---|---|---|
| 91 | N2_Mel06_P05_A2_D6TC | GGGTGGGAGGGGCGGGccctccCGCTTTTTTTTTTTGCGgg | 1.30 |
| 92 | N2_Mel13_P10_A0_D6TC | GGGTGGGAGGGGCGGGccgcccCCGccgccCCGTTTTTTTTTTTTCGG | 1.30 |
| 93 | N2_Mel13_P10_A0_D5TC | GGGTGGGAGGGGCGGGcgccccCGTTTTTTTTTTTTCGG | 1.30 |
| 94 | N2_Mel13_P06_A2_D5TC | GGGTGGGAGGGGCGGGccgccccCCGTTTTTTTTTTTCGGga | 1.30 |
| 95 | N2_Mel13_P09_A0_D6TC | GGGTGGGAGGGGCGGGccgccccCGTTTTTTTTTTTCGG | 1.30 |
| 96 | N2_Mel13_P02_A1_D5TC | GGGTGGGAGGGGCGGGccaccCCGTTTTTTTTTTTCGGg | 1.30 |
| 97 | N2_Mel13_P03_A1_D6TC | GGGTGGGAGGGGCGGGccaCCGTTTTTTTTTTTCGgt | 1.30 |
| 98 | N2_Mel13_P06_A1_D6TC | GGGTGGGAGGGGCGGGccctcCCGTTTTTTTTTTTCGGg | 1.30 |
| 99 | N2_Mel06_P03_A0_D7TC | GGGTGGGAGGGGCGGGcctccCCGTTTTTTTTTTTTGCGgg | 1.30 |
| 100 | N2_Mel06_P05_A2_D7TC | GGGTGGGAGGGGCGGGccgccCGTTTTTTTTTTTTCGGg | 1.30 |
| 101 | N2_Mel06_P09_A1_D6TC | GGGTGGGAGGGGCGGGccgccgCGTTTTTTTTTTTTGCGg | 1.30 |
| 102 | N1_Mel06_P10_A2_D6TC | GGGTGGGAGGGTCGGgcccgacCGGCTTTTTTTTTTTTGCGgt | 1.30 |
| 103 | N2_Mel06_P02_A0_D4TC | GGGTGGGAGGGGCGGGccacCGGCTTTTTTTTTTTCG | 1.30 |
| 104 | N2_Mel13_P01_A0_D5TC | GGGTGGGAGGGGCGGGccaccCCGTTTTTTTTTTTCGG | 1.29 |
| 105 | N2_Mel06_P03_A1_D5TC | GGGTGGGAGGGGCGGGcccaCaGCTTTTTTTTTTTCGGt | 1.29 |
| 106 | N2_Mel13_P09_A1_D7TC | GGGTGGGAGGGGCGGGccgccccgccCCGTTTTTTTTTTTTGCGgg | 1.29 |
| 107 | N2_Mel13_P01_A0_D5TC | GGGTGGGAGGGGCGGGccaccCCGTTTTTTTTTTTGCG | 1.29 |
| 108 | N2_Mel13_P06_A0_D5TC | GGGTGGGAGGGGCGGGccacctcCCGTTTTTTTTTTTCGG | 1.29 |
| 109 | N2_Mel13_P07_A1_D4TC | GGGTGGGAGGGGCGGGccctCCGTTTTTTTTTTTCGGa | 1.29 |

FIG. 4 (con't)

NUCLEIC ACID ELEMENT CANDIDATE MOLECULE AND SCREENING METHOD FOR SCREENING FOR NUCLEIC ACID ELEMENT FOR TARGET ANALYSIS USING THE SAME

CROSS-REFERENCE TO RELATED APPLICATIONS

This application is a national stage application of International Application No. PCT/JP2014/053664 entitled "Nucleic Acid Element Candidate Molecule and Screening Method for Screening for Nucleic Acid Element for Target Analysis Using the Same," filed on Feb. 17, 2014, which claims priority to Japanese Patent Application No. 2013-047341, filed on Mar. 8, 2013. The disclosures of each which are hereby incorporated by reference in their entirety.

TECHNICAL FIELD

The present invention relates to a nucleic acid element candidate molecule and a screening method for screening for a nucleic acid element for target analysis using the same.

BACKGROUND ART

It has been required in various fields such as clinical treatment, food, an environment, and the like to detect a target. Interactions with a target are generally utilized to detect the target. Among them, a method using an antibody that specifically binds to a target has been widely used. In this method, the target is bound to an antibody labeled with oxidoreductase such as peroxidase, for example. Then, a chromogenic reaction is performed by an enzyme in the labeled antibody using a chromogenic substrate. The target is indirectly subjected to analysis such as, for example, qualitative analysis or quantitative analysis by the detection of color development.

However, the antibody is obtained by immunization of animals. Thus, it is difficult to obtain a specific antigen to a highly toxic target or a low-molecular-weight target. Therefore, a nucleic acid molecule that binds to a target, i.e., a nucleic acid aptamer (hereinafter also referred to as an "aptamer") has received attention in recent years. The aptamer can be obtained in a test tube. Thus, for example, the aptamers to a toxic target and a low-molecular-weight target can be obtained.

In order to use such aptamer in detection of a target as a substitute for the antibody, it is attempted to use the aptamer in combination with DNAzyme that exhibits the same catalytic activity as in peroxidase. The DNAzyme generally has a guanine-rich structural motif and has a G-quadruplex structure and is DNA that exhibits a catalyst function of peroxidase by forming a complex through binding with hemin.

In the detection of a target, a single-stranded nucleic acid element obtained by linking a single-stranded aptamer and a single-stranded DNAzyme is specifically utilized (Non-Patent Document 1). The single-stranded nucleic acid element forms a stem structure by self-annealing in the absence of a target, and by the stem structure, the DNAzyme has a structure of not being capable of forming in G-quadruplex. Thus, in the absence of a target, DNAzyme in the single-stranded nucleic acid element cannot bind to hemin and thus cannot exhibit a catalyst function. On the other hand, in the presence of a target, the single-stranded nucleic acid element releases its stem structure by binding of the target to the aptamer. Thus, in the presence of a target, the DNAzyme in the single-stranded nucleic acid element forms G-quadruplex and exhibits a catalyst function by binding of the target to hemin. Therefore, when a chromogenic substrate to the redox activity is present together, a chromogenic reaction is generated in the presence of a target and is not generated in the absence of a target. Thus, the target can be analyzed by detecting the chromogenic reaction. Furthermore, it is not required to label the target, and thus, a wide range of targets including a low-molecular-weight substance and the like can be subjected to direct detection.

Therefore, a method in which DNAzyme superior in catalyst function and an aptamer showing superior binding force or superior specificity to the target are selected, and both are linked to produce a single-stranded nucleic acid element is employed. However, even when the selected DNAzyme and the selected aptamer are linked, it is really difficult to obtain a nucleic acid element suitable for practical use, for example, the nucleic acid element having a sufficient ratio (S/N) ratio between activity (S) in the presence of the target and activity (N) in the absence of the target. Therefore, it is unknown whether or not the element having sufficient S/N ratio is obtained even by modifying both of the DNAzyme and the aptamer to various sequences and producing a large number of nucleic acid element candidates from these combinations.

For these reasons, it is required to establish a method for simply and efficiently screening nucleic acid element candidate molecules for a single-stranded nucleic acid element superior in S/N ratio.

PRIOR ART DOCUMENT

Non-Patent Document

Non-Patent Document 1: Teller et. al., Anal. Chem., 2009, vol. 81, p. 9114-9119

SUMMARY OF INVENTION

Problem to be Solved by the Invention

Hence, the present invention is intended to provide a novel nucleic acid element candidate molecule for use in screening for a nucleic acid element for target analysis and a novel screening method for screening for a nucleic acid element for target analysis using the same.

Means for Solving Problem

The nucleic acid element candidate molecule according to the present invention is a nucleic acid element candidate molecule for use in screening for a nucleic acid element for target analysis, being either one of the single-stranded nucleic acids (I) and (II).

(I) A single-stranded nucleic acid including: a catalyst nucleic acid sequence (D) that exhibits a catalyst function; a blocking nucleic acid sequence (B); and a binding nucleic acid sequence (A) that binds to a target, linked in this order, wherein the blocking nucleic acid sequence (B) is complementary to a partial region (Dp) in the catalyst nucleic acid sequence (D), and a terminal region (Ab) on the blocking nucleic acid sequence (B) side in the binding nucleic acid sequence (A) is complementary to a flanking region (Df) of the partial region (Dp) in the catalyst nucleic acid sequence (D) and is complementary to a terminal region (Af) on the side opposite to the blocking nucleic acid sequence (B) side in the binding nucleic acid sequence (A).

(II) A single-stranded nucleic acid including: a catalyst nucleic acid sequence (D) that exhibits a catalyst function; a blocking nucleic acid sequence (B); a binding nucleic acid sequence (A) that binds to a target; and a stabilization nucleic acid sequence (S), linked in this order, wherein the blocking nucleic acid sequence (B) is complementary to a partial region (Dp) of the catalyst nucleic acid sequence (D), and a terminal region (Ba) on the binding nucleic acid sequence (A) side of the blocking nucleic acid sequence (B) is complementary to the stabilization nucleic acid sequence (S).

The screening method according to the present invention is a method for screening for a nucleic acid element for target analysis, including: measuring catalytic activity derived from the catalyst nucleic acid sequence (D) in at least one nucleic acid element candidate molecule according to the present invention in the presence and absence of a target to the binding nucleic acid sequence (A) in the at least one candidate molecule, and comparing the catalytic activity (S) in the presence of the target and the catalytic activity (N) in the absence of the target to select a candidate molecule showing a significant difference of the catalytic activity (S) in the presence of the target from the catalytic activity (N) in the absence of the target as the nucleic acid element for target analysis.

The production method according to the present invention is a method for producing a nucleic acid element for target analysis, including: selecting a nucleic acid element for target analysis from at least one nucleic acid element candidate molecule by the screening method according to the present invention.

Effects of the Invention

The candidate molecule according to the present invention allows a single-stranded nucleic acid element superior in S/N ratio to be simply and efficiently screened for. The nucleic acid element for target analysis, screened for as described above, is a technique really useful for researches and inspections in various fields such as, for example, clinical treatment, food, an environment, and the like.

BRIEF DESCRIPTION OF DRAWINGS

FIG. 1A is a schematic view showing the order of sequences in the candidate molecule. FIG. 1B is a schematic view showing a candidate molecule in the absence of a target. FIG. 1C is a schematic view showing the candidate molecule in the presence of a target.

FIG. 2A is a schematic view showing the order of sequences in the candidate molecule. FIG. 2B is a schematic view showing the candidate molecule in the absence of a target. FIG. 2C is a schematic view showing the candidate molecule in the presence of a target.

FIG. 3 is a table showing sequences of nucleic acid elements obtained in screening in Example of the present invention.

FIG. 4 is a table showing sequences of nucleic acid elements obtained in screening in Example of the present invention.

DESCRIPTION OF EMBODIMENTS

1. Nucleic Acid Element Candidate Molecule

Figure 1:
FIGS. 1A to 1C are schematic views showing an example of a candidate molecule according to the present invention.
Figure 1:
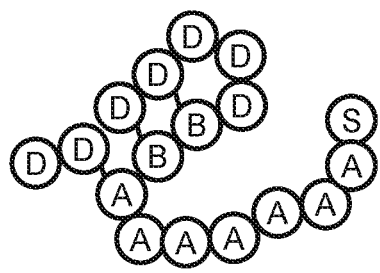
Figure 1:
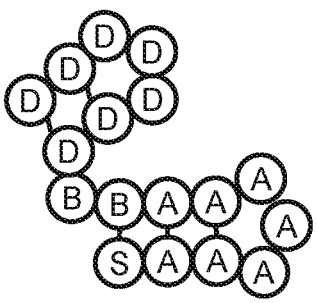

The candidate molecule according to the present invention is, as mentioned above, a nucleic acid element candidate molecule for use in screening for a nucleic acid element for target analysis, being either one of the single-stranded nucleic acids (I) and (II). Hereinafter, the nucleic acid element candidate molecule according to the present invention is also referred to as the "candidate molecule", and the nucleic acid sequence is also referred to as the "sequence".

The mechanism of the candidate molecule according to the present invention is assumed as follows and however is not limited thereby. A nucleic acid sequence is generally thermodynamically unstable among structures to be formed, and the abundance ratio of the nucleic acid sequence having a relatively stable structure is high. Moreover, it is known that the nucleic acid molecule such as DNAzyme is generally in more stable conformation by intramolecular annealing, and catalytic activity is exhibited by the conformation. It is also known that the nucleic acid molecule such as an aptamer is generally in more stable conformation by intramolecular annealing in the presence of a target and is bound to the target by the conformation. In the candidate molecule according to the present invention, as mentioned above, a part of the catalyst nucleic acid sequence (D) (hereinafter also referred to as a catalyst sequence (D)) and a part of the binding nucleic acid sequence (A) (hereinafter also referred to as the binding sequence (A)) have a relationship of being complementary to difference sequences, and stems can thus be formed. Thus, in the absence of a target, the formation of more stable conformation is blocked by the stem formed in the catalyst sequence (D), and accordingly, the exhibition of the catalyst function of the catalyst sequence (D) is inhibited (switched OFF), and the formation of more stable conformation is blocked by the stem formed in the binding sequence (A), and the structure in the state of not binding to the target is maintained. This state is hereinafter also referred to as a "blocking type". On the other hand, in the presence of a target, contact of the target to the binding sequence (A) causes a change of the binding sequence (A) to be in more stable conformation, and the stem in the binding sequence (A) is then released, and the target is bound to the binding sequence (A) in the conformation. The stem formed in the catalyst sequence (D) is also released by the more stable conformation of the binding sequence (A) caused by releasing of the stem formed in the binding sequence (A), and the catalyst sequence (D) is then in the conformation, and accordingly, the catalyst function of the catalyst sequence (D) is exhibited (switched ON). This state is hereinafter also referred to as an "activity type". Therefore, by using the candidate molecule according to the present invention as a candidate molecule for screening for a nucleic acid element for specific target analysis, a nucleic acid element that allows high-accuracy analysis with large difference in catalytic activity between the presence and absence of a target to be performed can be efficiently selected.

In the present invention, a sequence complementary to another sequence means, for example, a sequence that causes annealing with another sequence in the single-stranded nucleic acid. The annealing is also referred to as the "stem formation".

In the present invention, "complementary" is, for example, the complementation at the time when two kinds of sequences are aligned of, for example, 90% or more, preferably 95% or more, 96% or more, 97% or more, 98% or more, more preferably 99% or more, particularly preferably 100%, i.e., complete complementation.

The candidate molecule according to the present invention may be, for example, a molecule having or being composed of the single-stranded nucleic acid. In the candidate molecule according to the present invention, the single-stranded nucleic acid is, for example, at least one of the single-stranded nucleic acids (I) and (II) and may be both or either one of them.

As the candidate molecule according to the present invention, the single-stranded nucleic acids (I) and (II) are shown below. One of them can be described with reference to the description of the other unless otherwise shown.

(1) Single-Stranded Nucleic Acid (I)

The single-stranded nucleic acid (I) is, as mentioned above, a single-stranded nucleic acid including: a catalyst sequence (D) that exhibits a catalyst function; a blocking sequence (B); and a binding sequence (A) that binds to a target, linked in this order, wherein the blocking sequence (B) is complementary to a partial region (Dp) in the catalyst sequence (D), and a terminal region (Ab) on the blocking sequence (B) side in the binding sequence (A) is complementary to a flanking region (Df) of the partial region (Dp) in the catalyst sequence (D) and is complementary to a terminal region (Af) on the side opposite to the blocking sequence (B) side in the binding sequence (A).

The mechanism of the single-stranded nucleic acid (I) is assumed as follows, and the present invention, however, is not limited thereby. In the single-stranded nucleic acid (I), the partial region (Dp) of the catalyst sequence (D) is complementary to the blocking sequence (B), and the flanking region (Df) of the catalyst sequence (D) is complementary to the terminal region (Ab) of the binding sequence (A). Thus, in these complementary relationships, the stems can be formed. Thus, in the absence of a target, a stem between the partial region (Dp) of the catalyst sequence (D) and the blocking sequence (B) and a stem between the flanking region (Df) of the catalyst sequence (D) and the terminal region (Ab) of the binding sequence (A) are formed, thereby blocking formation of more stable conformation of the catalyst sequence (D). Accordingly, the exhibition of the catalyst function of the catalyst sequence (D) is inhibited (switched OFF), and the formation of the more stable conformation is blocked by the stem formed in the binding sequence (A), and the blocking-type structure in the state of not binding to the target is maintained. On the other hand, in the presence of a target, contact of the target to the binding sequence (A) causes a change of the binding sequence (A) to be in more stable conformation, and the stem formed in the binding sequence (A) is then released, and the target is bound to the binding sequence (A) changed to be in more stable conformation by intramolecular annealing. The stem formed in the catalyst sequence (D) is then released by the conformation of the binding sequence (A) caused by the releasing of the stem formed in the binding sequence (A), the catalyst sequence (D) is changed to be in more stable conformation by intramolecular annealing. Accordingly, the catalyst function of the catalyst sequence (D) is exhibited (switched ON).

The single-stranded nucleic acid (I) may further include a stabilization nucleic acid sequence (S) (hereinafter also referred to as the "stabilization sequence (S)), and in this case, the catalyst sequence (D), the blocking sequence (B), the binding sequence (A), and the stabilization sequence (S) are preferably linked in this order. In the case where the embodiment of the single-stranded nucleic acid having the stabilization sequence (S) is shown below as the candidate molecule according to the present invention, the stabilization sequence (S) is an optional sequence and may not be included in the embodiment.

The stabilization sequence (S) is, for example, a sequence for stabilizing the structure at the time when the binding sequence (A) binds to a target. The stabilization sequence (S) is, for example, complementary to the blocking sequence (B) or a part thereof and specifically preferably complementary to the terminal region (Ba) on the binding sequence (A) side in the blocking sequence (B). In this case, for example, when the conformation of the binding sequence (A) is formed by intramolecular annealing in the presence of the target, the stabilization sequence (S) linked to the binding sequence (A) and the terminal region (Ba) of the blocking sequence (B) linked to the binding sequence (A) form a stem. By forming such stem in the region linking to the binding sequence (A), the conformation of the binding sequence (A) binding to the target is more stabilized.

In the single-stranded nucleic acid (I), the order of the catalyst sequence (D), the blocking sequence (B), the binding sequence (A), and the optional stabilization sequence (S) is not limited to particular orders, and for example, they may be linked in this order from the 5' side or the 3' side, and the former is preferable. FIGS. 1A to 1C show schematic views of the single-stranded nucleic acid (I) in the state where these sequences are linked from the 5' side as an example of the candidate molecule according to the present invention. FIG. 1A is a schematic view showing the order of the sequences, FIG. 1B is a schematic view of the blocking type in the absence of a target, and FIG. 1C is a schematic view of the activity type in the presence of a target. In FIGS. 1A to 1C, D indicates a constituent unit (nucleotide) of the catalyst sequence (D), B indicates a constituent unit of the blocking sequence (B), A indicates a constituent unit of the binding sequence (A), S indicates a constituent unit of the stabilization sequence (S), and the line connecting between constituent units indicates binding. FIGS. 1A to 1C schematically show the sequences, the number of constituent units in each sequence (the length of each sequence) is not at all limited, and the stabilization sequence (S) is an optional sequence (the same applies hereinafter).

As shown in FIG. 1A, the example of the single-stranded nucleic acid (I) includes the catalyst sequence (D), the blocking sequence (B), the binding sequence (A), and the optional stabilization sequence (S) in this order. For example, as shown in FIG. 1B, in the absence of a target, a part of the catalyst sequence (D) binds to a part of the blocking sequence (B) and a part of the binding sequence (A) to form a stem, and the single-stranded nucleic acid (I) thus becomes a blocking-type single-stranded nucleic acid. On the other hand, for example, as shown in FIG. 1C, in the presence of a target, in the single-stranded nucleic acid (I), contact of the target to the binding sequence (A) causes formation of conformation of the binding sequence (A) by intramolecular annealing, and accordingly, the stem formed in the catalyst sequence (D) is released, and the conformation of the catalyst sequence (D) is formed by intramolecular annealing, and the catalyst sequence (D) exhibits the catalyst function. Moreover, as shown in FIG. 1C, for example, the conformation of the binding sequence (A) is more stabilized by binding of the blocking sequence (B) with the stabilization sequence (S).

In the single-stranded nucleic acid (I), the catalyst sequence (D), the blocking sequence (B), the binding sequence (A), and the optional stabilization sequence (S) may be linked indirectly with one another via spacer sequences, for example, and are preferably linked directly without the spacer sequences.

In the single-stranded nucleic acid (I), the catalyst sequence (D) is only required to be a sequence that exhibits a catalyst function. The catalyst function is not limited to particular functions and is, for example, a catalyst function in a redox reaction. The redox reaction may be, for example, a reaction in which electrons are transferred between two substrates in the process of generating a product from the substrates. The kind of the redox reaction is not limited to particular kinds. The catalyst function in the redox reaction can be, for example, the same activity as enzyme and can be, for example, specifically the same activity as peroxidase (hereinafter referred to as "peroxidase-like activity). The peroxidase activity can be, for example, horseradish peroxidase (HRP) activity. When the catalyst sequence (D) is a DNA sequence, it can be referred to as DNA enzyme or DNAzyme, and when the catalyst sequence (D) is an RNA sequence, it can be referred to as RNA enzyme or RNAzyme.

The catalyst sequence (D) is preferably a sequence that forms a G-quartet (or "G-tetrad") structure, more preferably a sequence that forms a guanine quartet (or "G-quadruplex") structure. The G-tetrad is, for example, a structure of guanine tetramers, and the G-quadruplex is, for example, a structure of a plurality of stacked G-tetrads. The G-tetrad and the G-quadruplex are, for example, formed in a nucleic acid having a G-rich structural motif by repetition. The G-tetrad can be, for example, a parallel-type or anti parallel-type G-tetrad and is preferably a parallel-type G-tetrad.

The catalyst sequence (D) is preferably a sequence that can bind to porphyrin and is specifically preferably a sequence that forms a G-tetrad and can bind to porphyrin. It is known that the sequence having a G-tetrad exhibits a catalyst function in a redox reaction by forming a complex with porphyrin by binding thereto, for example.

The porphyrin is not limited to particular porphyrins, and examples thereof include unsubstituted porphyrin and a derivative thereof. The derivative can be, for example, substituted porphyrin or a metal porphyrin obtained by forming a complex with a metal element. The substituted porphyrin can be, for example, N-methylmesoporphyrin. The metal porphyrin can be, for example, hemin that is a ferric complex. The porphyrin is, for example, preferably metal porphyrin, more preferably hemin.

The catalyst sequence (D) is not limited to particular sequences, and any sequence can be set. As specific examples, for example, a sequence of known catalyst nucleic acid molecule that exhibits a catalyst function or a partial sequence of the catalyst nucleic acid molecule can be employed. As a catalyst nucleic acid molecule having peroxidase activity, DNAzyme disclosed in the following literatures (1) to (4) and the like can be shown as examples, (1) Travascio et. al., Chem. Biol., 1998, vol. 5, p. 505-517,
(2) Cheng et. al., Biochimistry, 2009, vol. 48, p. 7817-7823,
(3) Teller et. al., Anal. Chem., 2009, vol. 81, p. 9114-9119,
(4) Tao et. al., Anal. Chem., 2009, vol. 81, p. 2144-2149.

Specific examples of the DNAzyme include molecules composed of base sequences of SEQ ID NOs: 110 to 115. The catalyst sequence (D) can be, for example, at least one base sequence selected from the group consisting of SEQ ID NOs: 110 to 115 or a partial sequence thereof.

EAD2
(SEQ ID NO: 110)
CTGGGAGGGAGGGAGGGA c-Myc
(SEQ ID NO: 111)
TGAGGGTGGGGAGGGTGGGGAA

PS2.M
(SEQ ID NO: 112)
GTGGGTAGGGCGGGTTGG

VEGF
(SEQ ID NO: 113)
GGGCGGGCCGGGGGCGGG

TA2
(SEQ ID NO: 114)
GGGGTTGGGGTGTGGGGTTGGGG

NECO0584
(SEQ ID NO: 115)
GGGTGGGAGGGTCGGG

The length of the catalyst sequence (D) is not limited to particular lengths, the lower limit is, for example, 12-mer, preferably 14-mer, more preferably 15-mer, the upper limit is, for example, 40-mer, preferably 30-mer, more preferably 20-mer, and the range is, for example, 12- to 40-mer, preferably 14- to 30-mer, more preferably 15- to 20-mer.

The complementation between the partial region (Dp) of the catalyst sequence (D) and the blocking sequence (B) is, for example, preferably 90% or more, more preferably 95% or more, 96% or more, 97% or more, 98% or more, yet more preferably 99% or more complementation, particularly preferably 100%, i.e., the complete complementation, between the blocking sequence (B) and the partial region (Dp).

The catalyst sequence (D) has a sequence complementary to the blocking sequence (B) and has a sequence complementary to a part of the binding sequence (A) as mentioned above. Moreover, the blocking sequence (B) is complementary to a part of the catalyst sequence (D) and is complementary to the stabilization sequence (S) when having the stabilization sequence (S) as mentioned above.

The sequence and the length of the blocking sequence (B) are not limited to particular sequences and lengths and can be set appropriately according to the sequence and the length of the catalyst sequence (D), for example.

The length of the blocking sequence (B) is not limited to particular lengths, the lower limit is, for example, 1-mer, preferably 2-mer, more preferably 3-mer, the upper limit is, for example, 20-mer, preferably 15-mer, more preferably 10-mer, and the range is, for example, 1- to 20-mer, preferably 2- to 15-mer, more preferably 3- to 10-mer.

As to the length of the partial region (Dp) of the catalyst sequence (D), the lower limit is, for example, 1-mer, preferably 2-mer, more preferably 3-mer, the upper limit is, for example, 20-mer, preferably 15-mer, more preferably 10-mer, and the range is, for example, 1- to 20-mer, preferably 2- to 15-mer, more preferably 3- to 10-mer. The length of the blocking sequence (B) and the length of the partial region (Dp) of the catalyst sequence (D) are, for example, preferably the same.

In the single-stranded nucleic acid (I), the position of the partial region (Dp) in the catalyst sequence (D), i.e., the annealing region of the blocking sequence (B) in the catalyst sequence (D) is not limited to particular positions. When the catalyst sequence (D), the blocking sequence (B), the binding sequence (A), and the optional stabilization sequence (S) are linked in this order, the conditions of the partial region (Dp) can be set as follows.

As to the length of the flanking region of the partial region (Dp) in the catalyst sequence (D), being a region (Db) between the terminal on the blocking sequence (B) side of the partial region (Dp) and the terminal on the catalyst sequence (D) side in the blocking sequence (B), the lower limit is, for example, 3-mer, preferably 4-mer, more preferably 5-mer, the upper limit is, for example, 40-mer, preferably 30-mer, more preferably 20-mer, and the range is, for example, 3- to 40-mer, preferably 4- to 30-mer, more preferably 5- to 20-mer.

As to the length of the flanking region of the partial region (Dp) in the catalyst sequence (D), being a region (Df) on the side opposite to the blocking sequence (B) side, the lower limit is, for example, 0-mer, preferably 1-mer, more preferably 2-mer, the upper limit is, for example, 40-mer, preferably 30-mer, more preferably 20-mer, and the range is, for example, 0- to 40-mer, preferably 1- to 30-mer, more preferably 2- to 20-mer.

As mentioned below, in the present invention, the target is not limited to particular targets, and a desired target can be selected. Thus, the binding sequence (A) can be designed according to the target. The binding sequence (A) set in the candidate molecule according to the present invention is preferably a sequence whose conformation changes by intramolecular annealing in the state of the binding sequence (A) alone in the presence of the target.

The length of the binding sequence (A) is not limited to particular lengths and is, for example, 12-mer, preferably 15-mer, more preferably 18-mer, the upper limit is, for example, 140-mer, preferably 80-mer, more preferably 60-mer, and the range is, for example, 12- to 140-mer, preferably 15- to 80-mer, more preferably 18- to 60-mer.

The terminal region (Ab) on the blocking sequence (B) side in the binding sequence (A) is, as mentioned above, complementary to the flanking region (Df) of the catalyst sequence (D). In this case, the terminal region (Ab) of the binding sequence (A) may be complementary to the entire flanking region (Df) of the catalyst sequence (D) or a partial region of the flanking region (Df). In the latter case, the terminal region (Ab) of the binding sequence (A) is preferably complementary to the terminal region on the partial region (Dp) side of the catalyst sequence (D) in the flanking region (Df).

The length of the terminal region (Ab) in the binding sequence (A), complementary to the flanking region (Df) of the catalyst sequence (D) is not limited to particular lengths, the lower limit is, for example, 1-mer, preferably 1-mer, more preferably 1-mer, the upper limit is, for example, 20-mer, preferably 8-mer, more preferably 3-mer, and the range is, for example, 1- to 20-mer, preferably 1- to 8-mer, more preferably 1- to 3-mer.

The stabilization sequence (S) is, as mentioned above, for example, complementary to the blocking sequence (B) or a part thereof and is specifically preferably complementary to the terminal region (Ba) on the binding sequence (A) side in the blocking sequence (B).

The sequence and the length of the stabilization sequence (S) are not limited to particular sequences and lengths and can be determined appropriately according to the sequence and the length of the blocking sequence (B), the sequence and the length of the binding sequence (A), and the like. As to the length of the stabilization sequence (S), the lower limit is, for example, 0-mer, preferably 1-mer, more preferably 1-mer, the upper limit is, for example, 10-mer, preferably 5-mer, more preferably 3-mer, and the range is, for example, 0- to 10-mer, preferably 1- to 5-mer, more preferably 1- to 3-mer. For example, when the stabilization sequence (S) is complementary to the entire blocking sequence (B), the length of the blocking sequence (B) is the same as that of the stabilization sequence (S). For example, when the stabilization sequence (S) is complementary to a part of the blocking sequence (B), the length of the part of the blocking sequence (B), for example, the terminal region (Ba) is the same as that of the stabilization sequence (S).

The full length of the single-stranded nucleic acid (I) is not limited to particular lengths, the lower limit is, for example, 25-mer, preferably 35-mer, more preferably 40-mer, the upper limit is, for example, 200-mer, preferably 120-mer, more preferably 80-mer, and the range is, for example, 25- to 200-mer, preferably 35- to 120-mer, more preferably 40- to 80-mer.

(2) Single-Stranded Nucleic Acid (II)

The single-stranded nucleic acid (II) is, as mentioned above, a single-stranded nucleic acid including: a catalyst sequence (D) that exhibits a catalyst function; a blocking sequence (B); a binding sequence (A) that binds to a target; and a stabilization sequence (S), linked in this order, wherein the blocking sequence (B) is complementary to a partial region (Dp) of the catalyst sequence (D), and a terminal region (Ba) on the binding sequence (A) side of the blocking sequence (B) is complementary to the stabilization sequence (S).

In the single-stranded nucleic acid (II), the binding sequence (A) is preferably a sequence that does not alone generate intramolecular annealing required to bind to a target. Moreover, it is preferred that, in the presence of a target, in the single-stranded nucleic acid (II), conformation is formed of all of the binding sequence (A), the terminal region (Ba), and the stabilization sequence (S) by annealing of the terminal region (Ba) of the blocking sequence (B) adjacent to the binding sequence (A) and the stabilization sequence (S).

The mechanism of the single-stranded nucleic acid (II) is assumed as follows, and the present invention, however, is not limited thereby. In the single-stranded nucleic acid (II), the partial region (Dp) of the catalyst sequence (D) is complementary to the blocking sequence (B), and thus, in this complementary relationship, the stem can be formed. Thus, in the absence of a target, a stem between the partial region (Dp) of the catalyst sequence (D) and the blocking sequence (B) is formed, thereby blocking formation of more stable conformation of the catalyst sequence (D). Accordingly, the exhibition of the catalyst function of the catalyst sequence (D) is inhibited (switched OFF). Moreover, the binding sequence (A) is a sequence that does not alone generate intramolecular annealing required to bind to a target, and thus, the formation of more stable conformation for binding to the target is blocked, and the state of not binding to the target is maintained. That is, the single-stranded nucleic acid (II) maintains the blocking-type structure in the absence of a target. On the other hand, in the presence of a target, contact of the target to the binding sequence (A) causes releasing of the stem formed between the terminal region (Ba) of the blocking sequence (B) and the partial region (Dp) of the catalyst sequence (D) in the process of changing the conformation of the binding sequence (A), and a stem is newly formed by annealing of the terminal region (Ba) of the blocking sequence (B) and the stabilization sequence (S). This stem serves as intramolecular annealing required for the binding sequence (A) to bind to the target, the conformation is formed of all of the stem and the binding sequence (A), and the target binds to the binding sequence (A). The releasing of the stem formed between the blocking sequence (B) and the catalyst sequence (D) then newly causes a change of the catalyst sequence (D) to be in more stable conformation by intramolecular annealing. Accordingly the catalyst function of the catalyst sequence (D) is exhibited (switched ON).

Figure 2:
FIGS. 2A to 2C are schematic views showing another example of a candidate molecule according to the present invention.
Figure 2:
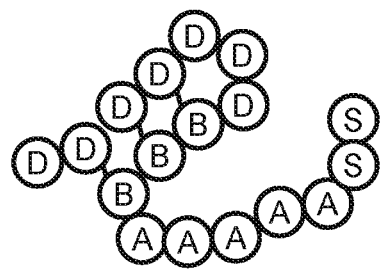
Figure 2:
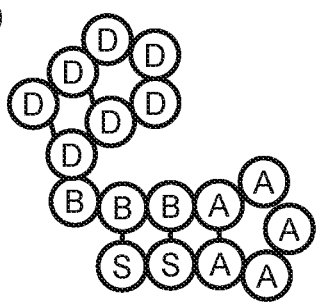

In the single-stranded nucleic acid (I), the order of the catalyst sequence (D), the blocking sequence (B), the binding sequence (A), and the stabilization sequence (S) is not limited to particular orders, and for example, they may be linked in this order from the 5' side or 3' side, and the former is preferable. FIGS. 2A to 2C show schematic views of the single-stranded nucleic acid (II) in the state where these sequences are linked from the 5' side as an example of the candidate molecule according to the present invention. FIG. 2A is a schematic view showing the order of the sequences, FIG. 2B is a schematic view of the blocking type in the absence of a target, FIG. 2C is a schematic view of the activity type in the presence of a target. In FIGS. 2A to 2C, D indicates a constituent unit (nucleotide) of the catalyst sequence (D), B indicates a constituent unit of the blocking sequence (B), A indicates a constituent unit of the binding sequence (A), S indicates a constituent unit of the stabilization sequence (S), and the line connecting between constituent units indicates binding. FIGS. 2A to 2C schematically show the sequences, and the number of constituent units in each sequence (the length of each sequence) is not at all limited (the same applies hereinafter).

As shown in FIG. 2A, the example of the single-stranded nucleic acid (II) includes the catalyst sequence (D), the blocking sequence (B), the binding sequence (A), and the stabilization sequence (S) in this order. For example, as shown in FIG. 2B, in the absence of a target, a part of the catalyst sequence (D) binds to the blocking sequence (B) to form a stem, and the single-stranded nucleic acid (II) thus becomes a blocking-type single-stranded nucleic acid. At that time, the binding sequence (A) does not form the conformation. On the other hand, for example, as shown in FIG. 2C, in the presence of a target, in the single-stranded nucleic acid (II), contact of the target to the binding sequence (A) causes releasing of the stem formed between the blocking sequence (B) and the catalyst sequence (D), a stem between the blocking sequence (B) and the stabilization sequence (S) is newly formed, and conformation is formed of the binding sequence (A), the blocking sequence (B), and the stabilization sequence (S). For example, the releasing of the stem formed between the blocking sequence (B) and the catalyst sequence (D) then causes formation of conformation of the catalyst sequence (D) by intramolecular annealing, and the catalyst sequence (D) exhibits a catalyst function. Moreover, as shown in FIG. 2C, for example, the conformation formed of the binding sequence (A), the blocking sequence (B), and the stabilization sequence (S) is more stabilized by binding of the blocking sequence (B) with the stabilization sequence (S).

The single-stranded nucleic acid (II) can be described with reference to the description of the single-stranded nucleic acid (I) unless otherwise shown. In the single-stranded nucleic acid (I), the catalyst sequence (D), the blocking sequence (B), and the stabilization sequence (S) are the same as those in the single-stranded nucleic acid (I), for example.

The binding sequence (A) is, for example, as mentioned above, a sequence that does not alone generates intramolecular annealing required to bind to a target, i.e., a sequence in which a stem is not formed in the molecule. The sequence and the length of the binding sequence (A) are not limited to particular sequences and lengths and are the same as those in the single-stranded nucleic acid (I) except that they are under the conditions where the intramolecular annealing required to bind to the target is not generated.

The blocking sequence (B) has a sequence complementary to the catalyst sequence (D) and a sequence complementary to the stabilization sequence (S) as mentioned above. Specifically, the blocking sequence (B) is complementary to the partial region (Dp) of the catalyst sequence (D), and the terminal region (Ba) on the binding sequence (A) side of the blocking sequence (B) is also complementary to the stabilization sequence (S).

In the blocking sequence (B), the length of the terminal region (Ba) complementary to the stabilization sequence (S) is not limited to particular lengths, the lower limit is, for example, 1-mer, preferably 1-mer, more preferably 1-mer, the upper limit is, for example, 15-mer, preferably 10-mer, more preferably 3-mer, and the range is, for example, 1- to 15-mer, 1- to 10-mer, preferably 1- to 5-mer, more preferably 1- to 3-mer.

The full length of the single-stranded nucleic acid (II) is not limited to particular lengths, the lower limit is, for example, 25-mer, preferably 35-mer, more preferably 40-mer, the upper limit is, for example, 200-mer, preferably 120-mer, more preferably 80-mer, and the range is, for example, 25- to 200-mer, preferably 35- to 120-mer, more preferably 40- to 80-mer.

In the candidate molecule according to the present invention, the target is not limited to particular targets, and any target can be selected. A nucleic acid sequence that binds to the target may be used as a binding sequence (A) in the candidate molecule according to the target. Examples of the target include a low-molecular-weight compound, microorganisms, virus, food allergen, a pesticide, and mycotoxin. Examples of the microorganisms include *Salmonella enterica, Listeria monocytogenes, Escherichia coli*, and mold, and the virus can be, for example, norovirus.

The candidate molecule according to the present invention is a molecule including a nucleotide residue and may be, for example, a molecule composed of only a nucleotide residue or a molecule including a nucleotide residue. Examples of the nucleotide include ribonucleotide, deoxyribonucleotide, and derivatives thereof. Specifically, the candidate molecule may be, for example, DNA including deoxyribonucleotide and/or a derivative thereof, RNA including ribonucleotide and/or a derivative thereof, or chimera (DNA/RNA) including the former and the latter.

The nucleotide may include either of a natural base (non-artificial base) and a non-natural base (artificial base) as a base, for example. Examples of the natural base include A, C, G, T, U and modified bases thereof. Examples of the modification include methylation, fluorination, amination, and thiation. Examples of the non-natural base include 2'-fluoropyrimidine and 2'-O-methylpyrimidine, and specific examples thereof include 2'-fluorouracil, 2'-aminouracil, 2'-O-methyluracil, and 2-thiouracil. The nucleotide may be, for example, a modified nucleotide, and examples of the modified nucleotide include 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil nucleotide residue, 2'-aminated-cytosine nucleotide residue, 2'-thiated-uracil nucleotide residue, and 2'-thiated-cytosine nucleotide residue. The candidate molecule may include non-nucleotide such as PNA (Peptide Nucleic Acid) or LNA (Locked Nucleic Acid), for example.

A linker sequence may be bound to either one of the terminals of the candidate molecule according to the present invention, for example. When the candidate molecule according to the present invention is used in the screening method described below, the candidate molecule may be in the state of being immobilized or in the state of not being immobilized (release state), for example. In the former case, the candidate molecule according to the present invention may be immobilized on the base material via the linker sequence. Examples of the base material (hereinafter also referred to as a "carrier") include containers such as a base plate, a bead, and a tube. The linker is, for example, a single-stranded nucleic acid sequence composed of the above-mentioned nucleotide and/or the above-mentioned non-nucleotide.

A method for immobilizing the candidate molecule is not limited to particular methods. Besides the immobilization via a linker sequence, for example, a known method for immobilizing a nucleic acid can be employed. The method can be, for example, a method utilizing photolithography and is specifically shown in U.S. Pat. No. 5,424,186 or the like. The method for immobilizing can be, for example, a method for synthesizing the candidate molecule on the base material. This method can be, for example, the spot method and is specifically shown in U.S. Pat. No. 5,807,522, JP H10-503841 A, or the like.

2. Screening Method

The screening method according to the present invention is, as mentioned above, a method for screening for a nucleic acid element for target analysis, including: measuring catalytic activity derived from the catalyst sequence (D) in at least one candidate molecule according to the present invention in the presence and absence of a target, and comparing the catalytic activity (S) in the presence of the target and the catalytic activity (N) in the absence of the target to select a candidate molecule showing a significant difference of the catalytic activity (S) in the presence of the target from the catalytic activity (N) in the absence of the target as the nucleic acid element for target analysis.

The screening method according to the present invention is characterized in that the candidate molecule according to the present invention is used, and other steps and conditions are not limited to particular steps and conditions.

It is preferred that, in the measuring, the catalytic activity derived from the catalyst sequence (D) is measured as a signal generated by the catalyst function of the catalyst sequence (D), for example. The signal is not limited to particular signals and can be, for example, an optical signal or an electrochemical signal. Examples of the optical signal include a chromogenic signal, a luminescent signal, and a fluorescent signal.

The signal is preferably generated from a substrate by the catalyst function of the catalyst sequence (D), for example. Thus, the measuring is preferably performed in the presence of a substrate according to the catalyst function of the catalyst sequence (D), for example.

Examples of the substrate include a substrate that generates a chromogenic product, light-emitting product, or fluorescent product by the catalyst function, a substrate that is a chromogenic, light-emitting, or fluorescent substrate and is a substrate that generates a product that quenches its color development, light emission, or fluorescence by the catalyst function, and a substrate that generates a different chromogenic product, light-emitting product or fluorescent product by the catalyst function. According to the substrate, for example, the catalyst function can be detected by observing the presence or absence of color development, light emission, or fluorescence or a change in, intensity of, or the like of color development, light emission, or fluorescence as a signal by visual check. Moreover, for example, the catalyst function can be detected by measuring the absorbance, reflectance, fluorescence intensity, or the like as a signal using an optical manner, for example. The catalyst function can be, for example, a catalyst function in a redox reaction.

When the catalyst sequence (D) has a catalyst function in the redox reaction, the substrate can be, for example, a substrate that can transfer electrons. In this case, a product of the substrate is generated from the catalyst sequence (D), for example, and in this process, electrons are transferred. This electron transfer can be electrochemically detected as an electrical signal by applying a voltage to an electrode, for example. The electrical signal can be detected by measuring the intensity of the electrical signal such as a current, for example.

The substrate is not limited to particular substrates, and examples thereof include hydrogen peroxide, 3,3',5,5'-Tetramethylbenzidine (TMB), 1,2-Phenylenediamine (OPD), 2,2'-Azinobis (3-ethylbenzothiazoline-6-sulfonic Acid Ammonium Salt (ABTS), 3,3'-Diaminobenzidine (DAB), 3,3'-Diaminobenzidine Tetrahydrochloride Hydrate (DAB4HCl), 3-Amino-9-ethylcarbazole (AEC), 4-Chloro-1-naphthol (4ClN), 2,4,6-Tribromo-3-hydroxybenzoic Acid, 2,4-Dichlorophenol, 4-Aminoantipyrine, 4-Aminoantipyrine Hydrochloride, and luminol.

In the measuring, the substrate may be supplied to the candidate molecule, for example, before, at the same time as, or after bringing the target into contact with the candidate molecule. It is preferred that the substrate is supplied to the candidate molecule as a substrate liquid mixed in a solvent, for example. The solvent is, for example, preferably a buffer solution such as Tris-HCl. The concentration of the substrate in the substrate liquid is not limited to particular concentrations and is, for example, 0.1 to 5 mmol/L, preferably 0.5 to 2 mmol/L. The pH of the substrate liquid is, for example, 6 to 9, preferably 6.8 to 9.

In the measuring, the conditions of the reaction caused by the catalyst sequence (D) are not limited to particular conditions. The temperature is, for example, 15° C. to 37° C., the time is, for example, 10 to 900 seconds.

In the measuring, porphyrin may be present together in addition to the substrate, for example. There is a known DNAzyme that exhibits higher redox activity by forming a complex with porphyrin, for example. Thus, in the screening method according to the present invention, porphyrin may be caused to be present together, and the redox activity may be detected as a complex between the catalyst sequence (D) and the porphyrin, for example. The supply of the porphyrin is not limited to particular supplies and can be performed at the same time as supplying the substrate.

The porphyrin is not limited to particular porphyrins, and examples thereof include unsubstituted porphyrin and a derivative thereof. The derivative can be, for example, substituted porphyrin or a metal porphyrin obtained by forming a complex with a metal element. The substituted porphyrin can be, for example, N-methylmesoporphyrin. The metal porphyrin can be, for example, hemin that is a ferric complex. The porphyrin is, for example, preferably metal porphyrin, more preferably hemin.

In the selecting in the screening method according to the present invention, for example, the comparison between the catalytic activity (S) in the presence of the target and the catalytic activity (N) in the absence of the target is preferably calculation of a ratio (S/N) between the catalytic activity (S) and the catalytic activity (N) For example, it is preferred that an S/N ratio is set in advance as an evaluation criteria, the nucleic acid element candidate molecule showing the ratio (S/N) higher than the reference value of a set ratio (S/N) is selected as the nucleic acid element for target analysis.

In the measuring in the screening method according to the present invention, the catalytic activity of each of a plurality of nucleic acid element candidate molecules having different sequences may be measured, for example. In this case, the candidate molecules preferably have different binding sequences (A) to the same target. In the selecting, it is preferred that the ratio (S/N) between the catalytic activity (S) in the presence of the target and the catalytic activity (N) in the absence of the target in each of the nucleic acid element candidate molecules is calculated, and a nucleic acid element candidate molecule having a relatively high ratio is selected as the nucleic acid element for target analysis. Accordingly, a nucleic acid element for target analysis, suitable for target analysis, can be easily selected among the plurality of candidate molecules to a predetermined target.

In the screening method according to the present invention, the candidate molecule may be used in the state of being immobilized or in the state of being released. In the former case, for example, the candidate molecule may be used in the state of being immobilized on a base material such as a container. In the latter case, for example, the candidate molecule may be used in the state of being in a container.

The screening method according to the present invention can be performed using a device for screening in which the candidate molecule is arranged. The device for screening includes, for example, the base material, the candidate molecule according to the present invention, and a detection section, the candidate molecule and the detection section are arranged in the base material, and the detection section is a detection section in which the catalyst function of the catalyst sequence (D) in the candidate molecule is detected.

A method for arranging the candidate molecule in the device for screening is not limited to particular methods, and the candidate molecule may or may not be immobilized on the base material, for example. In the former case, the candidate molecule may be directly or indirectly immobilized on the base material. The immobilization is not limited to particular immobilizations and can be described with reference to the description above.

A site of the base material, at which the candidate molecule is arranged, is not limited to particular sites, and for example, the candidate molecule is arranged in the detection section.

The device for screening may further include a regent section, for example. The reagent section may be arranged in the detection section, for example. In the reagent section, a reagent may be arranged in advance or may be supplied at the time of use, for example. Examples of the reagent include the above-mentioned substrate, porphyrin, and the like.

In the device for screening, the detection section is, as mentioned above, a detection section in which the catalyst function of the catalyst sequence (D) is detected. The detection section is preferably a detection section in which a signal generated by the catalyst function of the catalyst sequence (D) is detected as the catalyst function of the catalyst sequence (D). The signal can be, for example, a signal from a substrate by a catalyst function of the catalyst sequence (D) as mentioned above. The signal can be, for example, the above-mentioned optical signal or electrochemical signal.

When the signal is an optical signal, the detection section is, for example, a section for detecting an optical signal, and examples of the detection section include sections for detecting absorbance, reflectance, fluorescence intensity, and the like.

When the signal is an electrochemical signal, the detection section has an electrode system, for example. In this case, the detection section can be formed by arranging an electrode system on the surface of a base material. A method for arranging an electrode is not limited to particular methods, and a known method can be employed, for example. Specific examples thereof include thin film-forming methods such as a vapor deposition method, a sputtering method, a screen printing method, and a plating method. The electrode may be arranged directly or indirectly in the base material, for example. The indirect arrangement can be, for example, an arrangement via another member.

The electrode system may include a working electrode and a counter electrode or may include a working electrode, a counter electrode, and a reference electrode, for example. The material of each electrode is not limited to particular materials, and examples thereof include platinum, silver, gold, and carbon. Examples of the working electrode and the counter electrode include a platinum electrode, a silver electrode, a gold electrode, and a carbon electrode, and the reference electrode can be, for example, a silver/silver chloride electrode. The silver/silver chloride electrode can be formed by laminating a silver chloride electrode on a silver electrode, for example.

When the device for screening includes the electrode system, the candidate molecule is preferably arranged in the electrode system, and is preferably arranged in the working electrode among the electrodes, for example. When the device for screening includes the electrode system and the reagent section, the reagent section is preferably arranged on the electrode system, for example.

The device for screening may include a plurality of detection sections. In this case, for example, it is preferred that, in the device for screening, the surface of the base material is divided into matrixes, and the regions of the respective matrixes include the above-mentioned detection sections. In the device for screening, the number of the candidate molecules arranged in one detection section is not limited to particular numbers.

The base material is not limited to particular base materials. The base material is preferably a base plate having a surface that has insulation properties. The base material may be, for example, a base plate composed of an insulation material or a base material having an insulation layer that is composed of an insulating material on the surface thereof. The insulating material is not limited to particular materials, and examples thereof include known materials such as glass, ceramics, insulating plastic, and paper. The insulating plastic is not limited to particular plastics, and examples thereof include a silicone resin, a polyimide resin, an epoxy resin, and a fluorine resin.

3. Production Method for Producing Nucleic Acid Element for Target Analysis

The production method according to the present invention is, as mentioned above, a method for producing a nucleic acid element for target analysis, including selecting a nucleic acid element for target analysis from at least one nucleic acid element candidate molecule by the screening method according to the present invention. The production method according to the present invention is characterized in that an intended nucleic acid element for target analysis is selected from the candidate molecules by the screening method according to the present invention, and other steps and conditions are not at all limited.

The present invention is described in more detail below with reference to the example and the like. The present invention, however, is not limited thereby.

EXAMPLE

Example 1

A plurality of nucleic acid element candidate molecules were produced, and nucleic acid elements for melanin analysis each having an S/N ratio higher than a publicly known nucleic acid element were screened for.

As the known nucleic acid element (K), a single-stranded nucleic acid element (K) including NECO 0584 (SEQ ID NO: 115) that is DNAzyme as a catalyst sequence (D) and a melamine aptamer (SEQ ID NO: 116) as a binding sequence (A) was used.

```
Melamine aptamer
                                  (SEQ ID NO: 116)
CGCTTTTTTTTTTTGCG

NECO 0584
                                  (SEQ ID NO: 115)
GGGTGGGAGGGTCGGG

Nucleic acid element (K)
                                  (SEQ ID NO: 117)
TGGGTGGGAGGGTCGGGCCCTCCCGCTTTTTTTTTTTGCGG
```

As nucleic acid element candidate molecules, 591 kinds satisfying the following conditions were provided. As a catalyst sequence (D), two kinds of 16-mer sequences were designed based on DNAzyme in the known nucleic acid element. As a binding sequence (A), three kinds of 19-mer sequences were designed based on the melamine aptamer in the known nucleic acid element. The length of a blocking sequence (B) and the length of a partial region (Dp) in the catalyst sequence (D) were the same of 0- to 7-mer. The length between the 3' end of the partial region (Dp) of the catalyst sequence (D) and the blocking sequence (B) was 0- to 16-mer. The length of an upstream region (Df) of the partial region (Dp) of the catalyst sequence (D) was 0- to 16-mer. The length of the stabilization sequence (S) was 0- to 3-mer.

As controls, two kinds of NECO 0584 (SEQ ID NO: 115) that is DNAzyme of a positive control (PC) and reverse NC1 (SEQ ID NO: 118) that is DNAzyme of a negative control (NC) were used.

```
Positive control NECO 0584
                                  (SEQ ID NO: 115)
GGGTGGGAGGGTCGGG Negative control NC1
                                  (SEQ ID NO: 118)
CCCACCCTCCCAGCCC
```

Each 10 spots of the candidate molecules, the known nucleic acid element (K), and the controls (PC, NC) were randomly immobilized on the microarray chip (trade name: ElectraSense 12K microarray chip, CustomArray) to synthesize an array chip. 130 μL of a reagent A having the following composition was then added to the array chip, which was thereafter reacted at room temperature for 1 hour in the presence or absence of melamine. After the reaction, the reagent A was removed from the array chip, and 130 μL of a reagent B containing hydrogen peroxide (Wako Pure Chemical Industries, Ltd.) as a substrate and a ferrocene methyl alcohol (FMA, Tokyo Chemical Industry Co., Ltd.) as a mediator for redox reaction, having the following composition, was added thereto. An electrical signal generated by the redox reaction in the array chip was measured as a current. The measurement was performed using a measurement device (product name: ElectraSense Reader, CombiMatrix). The composition of DNAzyme buffer in each of the following reagents A and B includes Tris-HCl (pH7.4), 20 mmol/L KCl, and 0.05% Triton X-100.

TABLE 1

| (Composition of reagent A) |
| --- |
| 5 μmol/L Hemin (Sigma-Aldrich) |
| 0 or 5 mmol/L Melamine (melamine reference standard, Wako Pure Chemical Industries, Ltd.) |
| 1 × DNAzyme buffer |
| (Composition of reagent B) |
| 5 μmol/L Hemin (Sigma-Aldrich) |
| 0 or 5 mmol/L Melamine (melamine reference standard, Wako Pure Chemical Industries, Ltd.) |
| 2 mmol/L Substrate (hydrogen peroxide) |
| 0.1 mg/mL Mediator |
| 1 × DNAzyme buffer |

Each ratio (S/N ratio) between a current value (S) in the presence of melamine and a current value (N) in the absence of melamine was then calculated. The results of the controls showed S/N ratios (0.88 to 1.05) lower than the S/N ratio of the known nucleic acid element (K). In contrast, the results of 109 candidate molecules shown in FIGS. 3 and 4 showed S/N ratios higher than the S/N ratio (1.289) of the known nucleic acid element (K). In each of the sequences shown in FIGS. 3 and 4, from the 5' side, a sequence indicated by capital letters is DNAzyme (D), a sequence indicated by lower-case letters is a blocking sequence (B), a sequence indicated by capital letters is an aptamer (A), and a sequence indicated by lower-case letters is a stabilization sequence (S).

Among the 590 candidate molecules, 109 candidate molecules showed S/N ratios higher than that of the known nucleic acid element (K). It is thus demonstrated that nucleic acid elements having S/N ratios superior than that of the known nucleic acid element can be screened for at about ⅕ probability by employing the designs of the candidate molecules according to the present invention.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese patent application No. 2013-47341, filed on Mar. 8, 2013, the disclosure of that is incorporated herein its entirety by reference.

INDUSTRIAL APPLICABILITY

The candidate molecule according to the present invention allows a single-stranded nucleic acid element superior in S/N ratio to be simply and efficiently screened for. The nucleic acid element for target analysis, screened for as described above, is a technique really useful for researches and inspections in various fields such as, for example, clinical treatment, food, an environment, and the like.

SEQUENCE LISTING

TF14001WO_ST25.txt

The invention claimed is:

1. A nucleic acid element candidate molecule for use in screening for a nucleic acid element for target analysis, being either one of single-stranded nucleic acids (I) and (II):
   (I) a single-stranded nucleic acid comprising:
      a catalyst nucleic acid sequence (D) that exhibits a catalyst function, wherein the catalyst nucleic acid sequence (D) is DNAzyme with HRP-mimicking activity;
      a blocking nucleic acid sequence (B); and
      a binding nucleic acid sequence (A) that binds to a target, linked in this order, wherein
      the blocking nucleic acid sequence (B) is complementary to a partial region (Dp) in the catalyst nucleic acid sequence (D), and
      a terminal region (Ab) on the blocking nucleic acid sequence (B) side in the binding nucleic acid sequence (A) is complementary to a flanking region (Df) of the partial region (Dp) in the catalyst nucleic acid sequence (D) and is complementary to a terminal region (Af) on the side opposite to the blocking nucleic acid sequence (B) side in the binding nucleic acid sequence (A), wherein in the absence of a target, a stem between the partial region (Dp) of the catalyst nucleic acid sequence (D) and the blocking nucleic acid sequence (B) and a stem between the flanking region (Df) of the catalyst nucleic acid sequence (D) and the terminal region (Af) of the binding nucleic acid sequence (A) are formed, thereby inhibiting the catalyst function of the catalyst nucleic acid sequence (D); and
   (II) a single-stranded nucleic acid comprising:
      a catalyst nucleic acid sequence (D) that exhibits a catalyst function, wherein the catalyst nucleic acid sequence (D) is DNAzyme with HRP-mimicking activity;
      a blocking nucleic acid sequence (B);
      a binding nucleic acid sequence (A) that binds to a target; and
      a stabilization nucleic acid sequence (S), linked in this order, wherein
      the blocking nucleic acid sequence (B) is complementary to a partial region (Dp) of the catalyst nucleic acid sequence (D), and
      a terminal region (Ba) on the binding nucleic acid sequence (A) side of the blocking nucleic acid sequence (B) is complementary to the stabilization nucleic acid sequence (S), wherein in the absence of a target, a stem between the partial region (Dp) of the catalyst nucleic acid sequence (D) and the blocking nucleic acid sequence (B) and a stem between the flanking region (Df) of the catalyst nucleic acid sequence (D) and the terminal region (Ba) of the blocking nucleic acid sequence (B) are formed, thereby inhibiting the catalyst function of the catalyst nucleic acid sequence (D).

2. The nucleic acid element candidate molecule according to claim 1, wherein
   the catalyst nucleic acid sequence (D), the blocking nucleic acid sequence (B), and the binding nucleic acid sequence (A) are linked from the 5' side in this order.

3. The nucleic acid element candidate molecule according to claim 1, wherein
   the length of the catalyst nucleic acid sequence (D) is 12- to 40-mer.

4. The nucleic acid element candidate molecule according to claim 1, wherein
   the catalyst nucleic acid sequence (D) is at least one base sequence selected from the group consisting of SEQ ID NOs: 110 to 115 or a partial sequence thereof,

```
EAD2
                                          (SEQ ID NO: 110)
CTGGGAGGGAGGGAGGGA, c-Myc
                                          (SEQ ID NO: 111)
TGAGGGTGGGGAGGGTGGGGAA,

PS2.M
                                          (SEQ ID NO: 112)
GTGGGTAGGGCGGGTTGG,

VEGF
                                          (SEQ ID NO: 113)
GGGCGGGCCGGGGCGGG,

TA2
                                          (SEQ ID NO: 114)
GGGGTTGGGGTGTGGGGTTGGGG,

NECO0584
                                          (SEQ ID NO: 115)
GGGTGGGAGGGTCGGG.
```

5. The nucleic acid element candidate molecule according to claim 1, wherein
   the length of the blocking nucleic acid sequence (B) is 1- to 20-mer, and
   the length of the partial region (Dp) in the catalyst nucleic acid sequence (D) is 1- to 20-mer.

6. The nucleic acid element candidate molecule according to claim 1, wherein
   the length of a region (Db) between the terminal on the blocking nucleic acid sequence (B) side of the partial region (Dp) in the catalyst nucleic acid sequence (D) and the terminal on the catalyst nucleic acid sequence (D) side in the blocking nucleic acid sequence (B), being a flanking region of the partial region (Dp) in the catalyst nucleic acid sequence (D), is 3- to 40-mer.

7. The nucleic acid element candidate molecule according to claim 1, wherein
   the length of the region (Df) on the side opposite to the blocking nucleic acid sequence (B) side, being a flanking region of the partial region (Dp) in the catalyst nucleic acid sequence (D), is 0- to 40-mer.

8. The nucleic acid element candidate molecule according to claim 1, wherein the length of the binding nucleic acid sequence (A) is 12- to 140-mer.

9. The nucleic acid element candidate molecule according to claim 1, wherein
the single-stranded nucleic acid is the single-stranded nucleic acid (I) and further comprises a stabilization nucleic acid sequence (S), wherein
the catalyst nucleic acid sequence (D), the blocking nucleic acid sequence (B), the binding nucleic acid sequence (A), and the stabilization nucleic acid sequence (S) are linked in this order.

10. The nucleic acid element candidate molecule according to claim 9, wherein
the stabilization nucleic acid sequence (S) is complementary to the terminal region (Ba) on the binding nucleic acid sequence (A) side in the blocking nucleic acid sequence (B).

11. The nucleic acid element candidate molecule according to claim 9, wherein
the length of the stabilization nucleic acid sequence (S) is 1- to 10-mer.

12. The nucleic acid element candidate molecule according to claim 1, wherein
the single-stranded nucleic acid is the single-stranded nucleic acid (II), and
the length of the stabilization nucleic acid sequence (S) is 1- to 10-mer.

13. A screening method for screening for a nucleic acid element for target analysis, comprising:
measuring catalytic activity derived from the catalyst nucleic acid sequence (D) in at least one nucleic acid element candidate molecule according to claim 1 in the presence and absence of a target,
comparing the catalytic activity (S) in the presence of the target and the catalytic activity (N) in the absence of the target, and
selecting a nucleic acid element candidate molecule showing a significant difference of the catalytic activity (S) in the presence of the target from the catalytic activity (N) in the absence of the target as the nucleic acid element for target analysis,
wherein the catalytic activity (S) in the presence of the target is higher than the catalytic activity (N) in the absence of the target.

14. The screening method according to claim 13, wherein
the at least one nucleic acid element candidate molecule comprises a plurality of the nucleic acid element candidate molecules,
in the measuring, catalytic activity of the nucleic acid element candidate molecules, having different sequences, is measured, and
in the selecting, the ratio (S/N) between the catalytic activity (S) in the presence of the target and the catalytic activity (N) in the absence of the target in the plurality of the nucleic acid element candidate molecules is calculated, and a nucleic acid element candidate molecule having a relatively high ratio is selected as the nucleic acid element for target analysis.

15. The screening method according to claim 13, wherein the signal is an optical signal or an electrochemical signal.

16. The screening method according to claim 13, wherein the catalytic activity is measured in the presence of a substrate to the catalyst function of the catalyst nucleic acid sequence (D).

* * * * *

```
                          SEQUENCE LISTING

<160> NUMBER OF SEQ ID NOS: 118

<210> SEQ ID NO 1
<211> LENGTH: 42
<212> TYPE: DNA
<213> ORGANISM: Artificial Sequence
<220> FEATURE:
<223> OTHER INFORMATION: nucleic acid element

<400> SEQUENCE: 1
gggtgggagg ggcgggctcc caccgctttt ttttttttgc gg                42

<210> SEQ ID NO 2
<211> LENGTH: 39
<212> TYPE: DNA
<213> ORGANISM: Artificial Sequence
<220> FEATURE:
<223> OTHER INFORMATION: nucleic acid element

<400> SEQUENCE: 2
gggtgggagg ggcgggctcc cgctttttt tttttgcgg                    39

<210> SEQ ID NO 3
<211> LENGTH: 42
<212> TYPE: DNA
<213> ORGANISM: Artificial Sequence
<220> FEATURE:
<223> OTHER INFORMATION: nucleic acid element

<400> SEQUENCE: 3
gggtgggagg ggcgggctcc caccgtttttt tttttttcgg tg              42

<210> SEQ ID NO 4
<211> LENGTH: 41
<212> TYPE: DNA
<213> ORGANISM: Artificial Sequence
<220> FEATURE:
<223> OTHER INFORMATION: nucleic acid element

<400> SEQUENCE: 4
gggtgggagg ggcgggccct ccgctttttt tttttgcgg a                 41

<210> SEQ ID NO 5
<211> LENGTH: 40
<212> TYPE: DNA
<213> ORGANISM: Artificial Sequence
<220> FEATURE:
<223> OTHER INFORMATION: nucleic acid element

<400> SEQUENCE: 5
gggtgggagg ggcgggctcc caccgttttt tttttttcgg                  40

<210> SEQ ID NO 6
<211> LENGTH: 38
<212> TYPE: DNA
<213> ORGANISM: Artificial Sequence
<220> FEATURE:
<223> OTHER INFORMATION: nucleic acid element

<400> SEQUENCE: 6
gggtgggagg ggcgggctcc ccgtttttttt tttttcgg                   38
```

<210> SEQ ID NO 7
<211> LENGTH: 42
<212> TYPE: DNA
<213> ORGANISM: Artificial Sequence
<220> FEATURE:
<223> OTHER INFORMATION: nucleic acid element

<400> SEQUENCE: 7
gggtgggagg ggcgggctcc cacgcttttt tttttttgcg tg          42

<210> SEQ ID NO 8
<211> LENGTH: 40
<212> TYPE: DNA
<213> ORGANISM: Artificial Sequence
<220> FEATURE:
<223> OTHER INFORMATION: nucleic acid element

<400> SEQUENCE: 8
gggtgggagg ggcgggccac ccgcttttttt tttttgcgg          40

<210> SEQ ID NO 9
<211> LENGTH: 40
<212> TYPE: DNA
<213> ORGANISM: Artificial Sequence
<220> FEATURE:
<223> OTHER INFORMATION: nucleic acid element

<400> SEQUENCE: 9
gggtgggagg ggcgggcctc ccgcttttttt tttttgcgg          40

<210> SEQ ID NO 10
<211> LENGTH: 42
<212> TYPE: DNA
<213> ORGANISM: Artificial Sequence
<220> FEATURE:
<223> OTHER INFORMATION: nucleic acid element

<400> SEQUENCE: 10
gggtgggagg ggcgggcctc ccacgctttt tttttttgc gt          42

<210> SEQ ID NO 11
<211> LENGTH: 40
<212> TYPE: DNA
<213> ORGANISM: Artificial Sequence
<220> FEATURE:
<223> OTHER INFORMATION: nucleic acid element

<400> SEQUENCE: 11
gggtgggagg ggcgggctcc cacgcttttt tttttttgcg          40

<210> SEQ ID NO 12
<211> LENGTH: 38
<212> TYPE: DNA
<213> ORGANISM: Artificial Sequence
<220> FEATURE:
<223> OTHER INFORMATION: nucleic acid element

<400> SEQUENCE: 12
gggtgggagg ggcgggctcc cgcttttttt ttttttgcg          38

<210> SEQ ID NO 13
<211> LENGTH: 40
<212> TYPE: DNA
<213> ORGANISM: Artificial Sequence
<220> FEATURE:
<223> OTHER INFORMATION: nucleic acid element

```
<400> SEQUENCE: 13
gggtgggagg ggcgggccct ccgcttttttt tttttttgcgg                    40

<210> SEQ ID NO 14
<211> LENGTH: 40
<212> TYPE: DNA
<213> ORGANISM: Artificial Sequence
<220> FEATURE:
<223> OTHER INFORMATION: nucleic acid element

<400> SEQUENCE: 14
gggtgggagg ggcgggcctc cgcttttttt tttttgcgga                     40

<210> SEQ ID NO 15
<211> LENGTH: 38
<212> TYPE: DNA
<213> ORGANISM: Artificial Sequence
<220> FEATURE:
<223> OTHER INFORMATION: nucleic acid element

<400> SEQUENCE: 15
gggtgggagg ggcgggctcc gcttttttttt ttttgcgg                      38

<210> SEQ ID NO 16
<211> LENGTH: 40
<212> TYPE: DNA
<213> ORGANISM: Artificial Sequence
<220> FEATURE:
<223> OTHER INFORMATION: nucleic acid element

<400> SEQUENCE: 16
gggtgggagg ggcgggccca ccgcttttttt tttttttgcgg                   40

<210> SEQ ID NO 17
<211> LENGTH: 41
<212> TYPE: DNA
<213> ORGANISM: Artificial Sequence
<220> FEATURE:
<223> OTHER INFORMATION: nucleic acid element

<400> SEQUENCE: 17
gggtgggagg ggcgggcctc ccgcttttttt tttttttgcgg g                 41

<210> SEQ ID NO 18
<211> LENGTH: 42
<212> TYPE: DNA
<213> ORGANISM: Artificial Sequence
<220> FEATURE:
<223> OTHER INFORMATION: nucleic acid element

<400> SEQUENCE: 18
gggtgggagg ggcgggcccc tccgcttttttt tttttttgcg ga                42

<210> SEQ ID NO 19
<211> LENGTH: 38
<212> TYPE: DNA
<213> ORGANISM: Artificial Sequence
<220> FEATURE:
<223> OTHER INFORMATION: nucleic acid element

<400> SEQUENCE: 19
gggtgggagg ggcgggcctc cgcttttttttt ttttgcg                      38

<210> SEQ ID NO 20
```

```
<211> LENGTH: 41
<212> TYPE: DNA
<213> ORGANISM: Artificial Sequence
<220> FEATURE:
<223> OTHER INFORMATION: nucleic acid element

<400> SEQUENCE: 20
gggtgggagg ggcgggtccc accgcttttt tttttttgcg g                         41

<210> SEQ ID NO 21
<211> LENGTH: 37
<212> TYPE: DNA
<213> ORGANISM: Artificial Sequence
<220> FEATURE:
<223> OTHER INFORMATION: nucleic acid element

<400> SEQUENCE: 21
gggtgggagg ggcgggctcc cgttttttttt ttttcgg                              37

<210> SEQ ID NO 22
<211> LENGTH: 40
<212> TYPE: DNA
<213> ORGANISM: Artificial Sequence
<220> FEATURE:
<223> OTHER INFORMATION: nucleic acid element

<400> SEQUENCE: 22
gggtgggagg ggcgggcctc ccgttttttt tttttcggga                            40

<210> SEQ ID NO 23
<211> LENGTH: 41
<212> TYPE: DNA
<213> ORGANISM: Artificial Sequence
<220> FEATURE:
<223> OTHER INFORMATION: nucleic acid element

<400> SEQUENCE: 23
gggtgggagg ggcgggcctc cccgttttttt tttttcggg g                          41

<210> SEQ ID NO 24
<211> LENGTH: 38
<212> TYPE: DNA
<213> ORGANISM: Artificial Sequence
<220> FEATURE:
<223> OTHER INFORMATION: nucleic acid element

<400> SEQUENCE: 24
gggtgggagg ggcgggcctc ccgttttttt tttttcgg                              38

<210> SEQ ID NO 25
<211> LENGTH: 39
<212> TYPE: DNA
<213> ORGANISM: Artificial Sequence
<220> FEATURE:
<223> OTHER INFORMATION: nucleic acid element

<400> SEQUENCE: 25
gggtgggagg ggcgggcctc cgcttttttt tttttgcgg                             39

<210> SEQ ID NO 26
<211> LENGTH: 40
<212> TYPE: DNA
<213> ORGANISM: Artificial Sequence
<220> FEATURE:
<223> OTHER INFORMATION: nucleic acid element

<400> SEQUENCE: 26
```
gggtgggagg ggcgggctcc cgcttttttt tttttgcggg          40

<210> SEQ ID NO 27
<211> LENGTH: 43
<212> TYPE: DNA
<213> ORGANISM: Artificial Sequence
<220> FEATURE:
<223> OTHER INFORMATION: nucleic acid element

<400> SEQUENCE: 27
gggtgggagg ggcgggcctc ccacgctttt ttttttttgc gtg       43

<210> SEQ ID NO 28
<211> LENGTH: 41
<212> TYPE: DNA
<213> ORGANISM: Artificial Sequence
<220> FEATURE:
<223> OTHER INFORMATION: nucleic acid element

<400> SEQUENCE: 28
gggtgggagg ggcgggcccc tccgcttttt tttttttgcg g         41

<210> SEQ ID NO 29
<211> LENGTH: 39
<212> TYPE: DNA
<213> ORGANISM: Artificial Sequence
<220> FEATURE:
<223> OTHER INFORMATION: nucleic acid element

<400> SEQUENCE: 29
gggtgggagg ggcgggcctc cccgtttttt tttttttcgg          39

<210> SEQ ID NO 30
<211> LENGTH: 39
<212> TYPE: DNA
<213> ORGANISM: Artificial Sequence
<220> FEATURE:
<223> OTHER INFORMATION: nucleic acid element

<400> SEQUENCE: 30
gggtgggagg ggcgggctcc ccgtttttttt tttttcggg          39

<210> SEQ ID NO 31
<211> LENGTH: 36
<212> TYPE: DNA
<213> ORGANISM: Artificial Sequence
<220> FEATURE:
<223> OTHER INFORMATION: nucleic acid element

<400> SEQUENCE: 31
gggtgggagg ggcgggctcc gtttttttttt tttcgg             36

<210> SEQ ID NO 32
<211> LENGTH: 41
<212> TYPE: DNA
<213> ORGANISM: Artificial Sequence
<220> FEATURE:
<223> OTHER INFORMATION: nucleic acid element

<400> SEQUENCE: 32
gggtgggagg ggcgggccac ccgcttttttt tttttgcgg g        41

<210> SEQ ID NO 33
<211> LENGTH: 37
<212> TYPE: DNA

```
<213> ORGANISM: Artificial Sequence
<220> FEATURE:
<223> OTHER INFORMATION: nucleic acid element

<400> SEQUENCE: 33
gggtgggagg ggcgggctcc gcttttttt ttttgcg                                    37

<210> SEQ ID NO 34
<211> LENGTH: 40
<212> TYPE: DNA
<213> ORGANISM: Artificial Sequence
<220> FEATURE:
<223> OTHER INFORMATION: nucleic acid element

<400> SEQUENCE: 34
gggtgggagg ggcgggccct cgcttttttt tttttgcgag                                40

<210> SEQ ID NO 35
<211> LENGTH: 41
<212> TYPE: DNA
<213> ORGANISM: Artificial Sequence
<220> FEATURE:
<223> OTHER INFORMATION: nucleic acid element

<400> SEQUENCE: 35
gggtgggagg ggcgggccac ccgtttttt tttttcgggt t                               41

<210> SEQ ID NO 36
<211> LENGTH: 41
<212> TYPE: DNA
<213> ORGANISM: Artificial Sequence
<220> FEATURE:
<223> OTHER INFORMATION: nucleic acid element

<400> SEQUENCE: 36
gggtgggagg ggcgggccct cccgcttttt ttttttgcg g                               41

<210> SEQ ID NO 37
<211> LENGTH: 42
<212> TYPE: DNA
<213> ORGANISM: Artificial Sequence
<220> FEATURE:
<223> OTHER INFORMATION: nucleic acid element

<400> SEQUENCE: 37
gggtgggagg ggcgggtccc accgcttttt ttttttgcg gt                              42

<210> SEQ ID NO 38
<211> LENGTH: 39
<212> TYPE: DNA
<213> ORGANISM: Artificial Sequence
<220> FEATURE:
<223> OTHER INFORMATION: nucleic acid element

<400> SEQUENCE: 38
gggtgggagg ggcgggctcc gcttttttt ttttgcgga                                  39

<210> SEQ ID NO 39
<211> LENGTH: 40
<212> TYPE: DNA
<213> ORGANISM: Artificial Sequence
<220> FEATURE:
<223> OTHER INFORMATION: nucleic acid element

<400> SEQUENCE: 39
gggtgggagg ggcgggcctc ccgtttttt tttttcggg                                  40
```

<210> SEQ ID NO 40
<211> LENGTH: 41
<212> TYPE: DNA
<213> ORGANISM: Artificial Sequence
<220> FEATURE:
<223> OTHER INFORMATION: nucleic acid element

<400> SEQUENCE: 40
gggtgggagg ggcgggtccc accgttttt tttttcggt g                    41

<210> SEQ ID NO 41
<211> LENGTH: 42
<212> TYPE: DNA
<213> ORGANISM: Artificial Sequence
<220> FEATURE:
<223> OTHER INFORMATION: nucleic acid element

<400> SEQUENCE: 41
gggtgggagg ggcggggccc ctccgctttt tttttttgc gg                  42

<210> SEQ ID NO 42
<211> LENGTH: 41
<212> TYPE: DNA
<213> ORGANISM: Artificial Sequence
<220> FEATURE:
<223> OTHER INFORMATION: nucleic acid element

<400> SEQUENCE: 42
gggtgggagg ggcgggccca cccgctttt tttttttgcg g                   41

<210> SEQ ID NO 43
<211> LENGTH: 41
<212> TYPE: DNA
<213> ORGANISM: Artificial Sequence
<220> FEATURE:
<223> OTHER INFORMATION: nucleic acid element

<400> SEQUENCE: 43
gggtgggagg ggcgggccct ccccgttttt tttttttcgg g                  41

<210> SEQ ID NO 44
<211> LENGTH: 40
<212> TYPE: DNA
<213> ORGANISM: Artificial Sequence
<220> FEATURE:
<223> OTHER INFORMATION: nucleic acid element

<400> SEQUENCE: 44
gggtgggagg gtcgggcccg acccttttt tttttttggt                    40

<210> SEQ ID NO 45
<211> LENGTH: 42
<212> TYPE: DNA
<213> ORGANISM: Artificial Sequence
<220> FEATURE:
<223> OTHER INFORMATION: nucleic acid element

<400> SEQUENCE: 45
gggtgggagg ggcgggtccc acccgctttt tttttttgc gg                  42

<210> SEQ ID NO 46
<211> LENGTH: 39
<212> TYPE: DNA
<213> ORGANISM: Artificial Sequence
<220> FEATURE:

<223> OTHER INFORMATION: nucleic acid element

<400> SEQUENCE: 46
gggtgggagg ggcgggcctc ccgctttttt tttttttgcg                                39

<210> SEQ ID NO 47
<211> LENGTH: 43
<212> TYPE: DNA
<213> ORGANISM: Artificial Sequence
<220> FEATURE:
<223> OTHER INFORMATION: nucleic acid element

<400> SEQUENCE: 47
gggtgggagg ggcggggccc ctccgctttt tttttttgc gga                            43

<210> SEQ ID NO 48
<211> LENGTH: 41
<212> TYPE: DNA
<213> ORGANISM: Artificial Sequence
<220> FEATURE:
<223> OTHER INFORMATION: nucleic acid element

<400> SEQUENCE: 48
gggtgggagg ggcgggctcc caccgctttt tttttttgc g                              41

<210> SEQ ID NO 49
<211> LENGTH: 42
<212> TYPE: DNA
<213> ORGANISM: Artificial Sequence
<220> FEATURE:
<223> OTHER INFORMATION: nucleic acid element

<400> SEQUENCE: 49
gggtgggagg ggcgggcccc tcccgctttt tttttttgc gg                             42

<210> SEQ ID NO 50
<211> LENGTH: 39
<212> TYPE: DNA
<213> ORGANISM: Artificial Sequence
<220> FEATURE:
<223> OTHER INFORMATION: nucleic acid element

<400> SEQUENCE: 50
gggtgggagg ggcgggcctc ccgtttttt ttttttcggg                                39

<210> SEQ ID NO 51
<211> LENGTH: 40
<212> TYPE: DNA
<213> ORGANISM: Artificial Sequence
<220> FEATURE:
<223> OTHER INFORMATION: nucleic acid element

<400> SEQUENCE: 51
gggtgggagg ggcgggccca ccgtttttt ttttttcggtg                               40

<210> SEQ ID NO 52
<211> LENGTH: 40
<212> TYPE: DNA
<213> ORGANISM: Artificial Sequence
<220> FEATURE:
<223> OTHER INFORMATION: nucleic acid element

<400> SEQUENCE: 52
gggtgggagg ggcgggcccc tccgtttttt tttttcgga                                40

```
<210> SEQ ID NO 53
<211> LENGTH: 42
<212> TYPE: DNA
<213> ORGANISM: Artificial Sequence
<220> FEATURE:
<223> OTHER INFORMATION: nucleic acid element

<400> SEQUENCE: 53
gggtgggagg ggcgggtccc accgtttttt tttttttcgg gt            42

<210> SEQ ID NO 54
<211> LENGTH: 37
<212> TYPE: DNA
<213> ORGANISM: Artificial Sequence
<220> FEATURE:
<223> OTHER INFORMATION: nucleic acid element

<400> SEQUENCE: 54
gggtgggagg ggcgggctcc gttttttttt tttcgga                  37

<210> SEQ ID NO 55
<211> LENGTH: 39
<212> TYPE: DNA
<213> ORGANISM: Artificial Sequence
<220> FEATURE:
<223> OTHER INFORMATION: nucleic acid element

<400> SEQUENCE: 55
gggtgggagg ggcgggccct cgcttttttt tttttgcga                39

<210> SEQ ID NO 56
<211> LENGTH: 40
<212> TYPE: DNA
<213> ORGANISM: Artificial Sequence
<220> FEATURE:
<223> OTHER INFORMATION: nucleic acid element

<400> SEQUENCE: 56
gggtgggagg ggcgggccac cgcttttttt tttttgcggt               40

<210> SEQ ID NO 57
<211> LENGTH: 41
<212> TYPE: DNA
<213> ORGANISM: Artificial Sequence
<220> FEATURE:
<223> OTHER INFORMATION: nucleic acid element

<400> SEQUENCE: 57
gggtgggagg ggcgggcccc tccgtttttt tttttttcgga g            41

<210> SEQ ID NO 58
<211> LENGTH: 41
<212> TYPE: DNA
<213> ORGANISM: Artificial Sequence
<220> FEATURE:
<223> OTHER INFORMATION: nucleic acid element

<400> SEQUENCE: 58
gggtgggagg ggcgggcccc tcgctttttt tttttttgcga g            41

<210> SEQ ID NO 59
<211> LENGTH: 42
<212> TYPE: DNA
<213> ORGANISM: Artificial Sequence
<220> FEATURE:
<223> OTHER INFORMATION: nucleic acid element
```

<400> SEQUENCE: 59
gggtgggagg ggcgggccca cccgcttttt tttttttgcg gg            42

<210> SEQ ID NO 60
<211> LENGTH: 38
<212> TYPE: DNA
<213> ORGANISM: Artificial Sequence
<220> FEATURE:
<223> OTHER INFORMATION: nucleic acid element

<400> SEQUENCE: 60
gggtgggagg ggcgggctcc cgttttttt ttttcggg                  38

<210> SEQ ID NO 61
<211> LENGTH: 42
<212> TYPE: DNA
<213> ORGANISM: Artificial Sequence
<220> FEATURE:
<223> OTHER INFORMATION: nucleic acid element

<400> SEQUENCE: 61
gggtgggagg ggcggggccc ctccgttttt ttttttcgg ag             42

<210> SEQ ID NO 62
<211> LENGTH: 40
<212> TYPE: DNA
<213> ORGANISM: Artificial Sequence
<220> FEATURE:
<223> OTHER INFORMATION: nucleic acid element

<400> SEQUENCE: 62
gggtgggagg ggcgggcccc tcgctttttt tttttgcga                40

<210> SEQ ID NO 63
<211> LENGTH: 40
<212> TYPE: DNA
<213> ORGANISM: Artificial Sequence
<220> FEATURE:
<223> OTHER INFORMATION: nucleic acid element

<400> SEQUENCE: 63
gggtgggagg ggcgggccct ccccgttttt ttttttcgg                40

<210> SEQ ID NO 64
<211> LENGTH: 39
<212> TYPE: DNA
<213> ORGANISM: Artificial Sequence
<220> FEATURE:
<223> OTHER INFORMATION: nucleic acid element

<400> SEQUENCE: 64
gggtgggagg ggcgggccac ccgttttttt ttttcggg                 39

<210> SEQ ID NO 65
<211> LENGTH: 42
<212> TYPE: DNA
<213> ORGANISM: Artificial Sequence
<220> FEATURE:
<223> OTHER INFORMATION: nucleic acid element

<400> SEQUENCE: 65
gggtgggagg gtcgggcccg acccgttttt tttttttcgg gt            42

<210> SEQ ID NO 66
<211> LENGTH: 38

<212> TYPE: DNA
<213> ORGANISM: Artificial Sequence
<220> FEATURE:
<223> OTHER INFORMATION: nucleic acid element

<400> SEQUENCE: 66
gggtgggagg ggcgggccca cgcttttttt tttttgcg                        38

<210> SEQ ID NO 67
<211> LENGTH: 40
<212> TYPE: DNA
<213> ORGANISM: Artificial Sequence
<220> FEATURE:
<223> OTHER INFORMATION: nucleic acid element

<400> SEQUENCE: 67
gggtgggagg ggcgggccct ccgttttttt tttttcggag                      40

<210> SEQ ID NO 68
<211> LENGTH: 40
<212> TYPE: DNA
<213> ORGANISM: Artificial Sequence
<220> FEATURE:
<223> OTHER INFORMATION: nucleic acid element

<400> SEQUENCE: 68
gggtgggagg ggcgggcccc tcccgtttttt ttttttttcgg                    40

<210> SEQ ID NO 69
<211> LENGTH: 38
<212> TYPE: DNA
<213> ORGANISM: Artificial Sequence
<220> FEATURE:
<223> OTHER INFORMATION: nucleic acid element

<400> SEQUENCE: 69
gggtgggagg ggcgggcctc cgttttttttt ttttcgga                       38

<210> SEQ ID NO 70
<211> LENGTH: 38
<212> TYPE: DNA
<213> ORGANISM: Artificial Sequence
<220> FEATURE:
<223> OTHER INFORMATION: nucleic acid element

<400> SEQUENCE: 70
gggtgggagg ggcgggccct ccgttttttt tttttcgg                        38

<210> SEQ ID NO 71
<211> LENGTH: 38
<212> TYPE: DNA
<213> ORGANISM: Artificial Sequence
<220> FEATURE:
<223> OTHER INFORMATION: nucleic acid element

<400> SEQUENCE: 71
gggtgggagg ggcgggccac ccgttttttt tttttcgg                        38

<210> SEQ ID NO 72
<211> LENGTH: 39
<212> TYPE: DNA
<213> ORGANISM: Artificial Sequence
<220> FEATURE:
<223> OTHER INFORMATION: nucleic acid element

<400> SEQUENCE: 72

```
gggtgggagg ggcgggccct ccgcttttttt tttttttgcg                   39
```

<210> SEQ ID NO 73
<211> LENGTH: 39
<212> TYPE: DNA
<213> ORGANISM: Artificial Sequence
<220> FEATURE:
<223> OTHER INFORMATION: nucleic acid element

<400> SEQUENCE: 73

```
gggtgggagg ggcgggcccc tcgcttttttt tttttttgcg                   39
```

<210> SEQ ID NO 74
<211> LENGTH: 43
<212> TYPE: DNA
<213> ORGANISM: Artificial Sequence
<220> FEATURE:
<223> OTHER INFORMATION: nucleic acid element

<400> SEQUENCE: 74

```
gggtgggagg ggcgggtccc acccgctttt ttttttttgc ggg                43
```

<210> SEQ ID NO 75
<211> LENGTH: 39
<212> TYPE: DNA
<213> ORGANISM: Artificial Sequence
<220> FEATURE:
<223> OTHER INFORMATION: nucleic acid element

<400> SEQUENCE: 75

```
gggtgggagg ggcgggccac cgcttttttt tttttgcgg                     39
```

<210> SEQ ID NO 76
<211> LENGTH: 41
<212> TYPE: DNA
<213> ORGANISM: Artificial Sequence
<220> FEATURE:
<223> OTHER INFORMATION: nucleic acid element

<400> SEQUENCE: 76

```
gggtgggagg ggcgggccac cccgttttttt tttttttcggg g                41
```

<210> SEQ ID NO 77
<211> LENGTH: 41
<212> TYPE: DNA
<213> ORGANISM: Artificial Sequence
<220> FEATURE:
<223> OTHER INFORMATION: nucleic acid element

<400> SEQUENCE: 77

```
gggtgggagg ggcgggtccc acgcttttttt tttttttgcgt g                41
```

<210> SEQ ID NO 78
<211> LENGTH: 39
<212> TYPE: DNA
<213> ORGANISM: Artificial Sequence
<220> FEATURE:
<223> OTHER INFORMATION: nucleic acid element

<400> SEQUENCE: 78

```
gggtgggagg ggcgggctcc cgttttttttt ttttcggga                    39
```

<210> SEQ ID NO 79
<211> LENGTH: 38
<212> TYPE: DNA
<213> ORGANISM: Artificial Sequence

```
<220> FEATURE:
<223> OTHER INFORMATION: nucleic acid element

<400> SEQUENCE: 79
gggtgggagg ggcgggccca ccgtttttttt ttttttcgg                              38

<210> SEQ ID NO 80
<211> LENGTH: 39
<212> TYPE: DNA
<213> ORGANISM: Artificial Sequence
<220> FEATURE:
<223> OTHER INFORMATION: nucleic acid element

<400> SEQUENCE: 80
gggtgggagg ggcgggccgc cgctttttttt tttttgcgg                              39

<210> SEQ ID NO 81
<211> LENGTH: 40
<212> TYPE: DNA
<213> ORGANISM: Artificial Sequence
<220> FEATURE:
<223> OTHER INFORMATION: nucleic acid element

<400> SEQUENCE: 81
gggtgggagg ggcgggcccc tccgcttttt tttttttgcg                              40

<210> SEQ ID NO 82
<211> LENGTH: 40
<212> TYPE: DNA
<213> ORGANISM: Artificial Sequence
<220> FEATURE:
<223> OTHER INFORMATION: nucleic acid element

<400> SEQUENCE: 82
gggtgggagg gtcgggcccg accgttttttt tttttttcgg                             40

<210> SEQ ID NO 83
<211> LENGTH: 38
<212> TYPE: DNA
<213> ORGANISM: Artificial Sequence
<220> FEATURE:
<223> OTHER INFORMATION: nucleic acid element

<400> SEQUENCE: 83
gggtgggagg ggcgggccct cgcttttttt ttttttgcg                               38

<210> SEQ ID NO 84
<211> LENGTH: 40
<212> TYPE: DNA
<213> ORGANISM: Artificial Sequence
<220> FEATURE:
<223> OTHER INFORMATION: nucleic acid element

<400> SEQUENCE: 84
gggtgggagg ggcgggctcc ccgtttttttt ttttttcgggg                            40

<210> SEQ ID NO 85
<211> LENGTH: 40
<212> TYPE: DNA
<213> ORGANISM: Artificial Sequence
<220> FEATURE:
<223> OTHER INFORMATION: nucleic acid element

<400> SEQUENCE: 85
gggtgggagg ggcgggccac cccgttttttt tttttttcggg                            40
```

<210> SEQ ID NO 86
<211> LENGTH: 42
<212> TYPE: DNA
<213> ORGANISM: Artificial Sequence
<220> FEATURE:
<223> OTHER INFORMATION: nucleic acid element

<400> SEQUENCE: 86
gggtgggagg gtcgggcccg acccgctttt tttttttgc gg                    42

<210> SEQ ID NO 87
<211> LENGTH: 42
<212> TYPE: DNA
<213> ORGANISM: Artificial Sequence
<220> FEATURE:
<223> OTHER INFORMATION: nucleic acid element

<400> SEQUENCE: 87
gggtgggagg ggcgggcgcc cctcgctttt tttttttgc ga                    42

<210> SEQ ID NO 88
<211> LENGTH: 39
<212> TYPE: DNA
<213> ORGANISM: Artificial Sequence
<220> FEATURE:
<223> OTHER INFORMATION: nucleic acid element

<400> SEQUENCE: 88
gggtgggagg gtcgggcccg acccttttt ttttttggg                        39

<210> SEQ ID NO 89
<211> LENGTH: 40
<212> TYPE: DNA
<213> ORGANISM: Artificial Sequence
<220> FEATURE:
<223> OTHER INFORMATION: nucleic acid element

<400> SEQUENCE: 89
gggtgggagg ggcgggccca cgcttttttt tttttgcgtg                      40

<210> SEQ ID NO 90
<211> LENGTH: 39
<212> TYPE: DNA
<213> ORGANISM: Artificial Sequence
<220> FEATURE:
<223> OTHER INFORMATION: nucleic acid element

<400> SEQUENCE: 90
gggtgggagg ggcgggcccc tccgttttt tttttttcgg                       39

<210> SEQ ID NO 91
<211> LENGTH: 42
<212> TYPE: DNA
<213> ORGANISM: Artificial Sequence
<220> FEATURE:
<223> OTHER INFORMATION: nucleic acid element

<400> SEQUENCE: 91
gggtgggagg ggcgggccct cccgctttt tttttttgcg gg                    42

<210> SEQ ID NO 92
<211> LENGTH: 40
<212> TYPE: DNA
<213> ORGANISM: Artificial Sequence
<220> FEATURE:
<223> OTHER INFORMATION: nucleic acid element

<400> SEQUENCE: 92
gggtgggagg ggcgggcccg ccccgttttt tttttttcgg                40

<210> SEQ ID NO 93
<211> LENGTH: 39
<212> TYPE: DNA
<213> ORGANISM: Artificial Sequence
<220> FEATURE:
<223> OTHER INFORMATION: nucleic acid element

<400> SEQUENCE: 93
gggtgggagg ggcgggccgc cccgtttttt tttttcgg                 39

<210> SEQ ID NO 94
<211> LENGTH: 41
<212> TYPE: DNA
<213> ORGANISM: Artificial Sequence
<220> FEATURE:
<223> OTHER INFORMATION: nucleic acid element

<400> SEQUENCE: 94
gggtgggagg ggcgggccct cccgttttttt tttttcggg a             41

<210> SEQ ID NO 95
<211> LENGTH: 40
<212> TYPE: DNA
<213> ORGANISM: Artificial Sequence
<220> FEATURE:
<223> OTHER INFORMATION: nucleic acid element

<400> SEQUENCE: 95
gggtgggagg ggcgggccgc ccccgttttt tttttttcgg               40

<210> SEQ ID NO 96
<211> LENGTH: 40
<212> TYPE: DNA
<213> ORGANISM: Artificial Sequence
<220> FEATURE:
<223> OTHER INFORMATION: nucleic acid element

<400> SEQUENCE: 96
gggtgggagg ggcgggccca cccgttttttt tttttcggg               40

<210> SEQ ID NO 97
<211> LENGTH: 38
<212> TYPE: DNA
<213> ORGANISM: Artificial Sequence
<220> FEATURE:
<223> OTHER INFORMATION: nucleic acid element

<400> SEQUENCE: 97
gggtgggagg ggcgggccac cgttttttttt ttttcggt                38

<210> SEQ ID NO 98
<211> LENGTH: 41
<212> TYPE: DNA
<213> ORGANISM: Artificial Sequence
<220> FEATURE:
<223> OTHER INFORMATION: nucleic acid element

<400> SEQUENCE: 98
gggtgggagg ggcgggcccc tcccgttttt tttttttcgg g             41

<210> SEQ ID NO 99

<210> SEQ ID NO 99
<211> LENGTH: 41
<212> TYPE: DNA
<213> ORGANISM: Artificial Sequence
<220> FEATURE:
<223> OTHER INFORMATION: nucleic acid element

<400> SEQUENCE: 99
gggtgggagg ggcgggcctc ccacgctttt tttttttgc g          41

<210> SEQ ID NO 100
<211> LENGTH: 43
<212> TYPE: DNA
<213> ORGANISM: Artificial Sequence
<220> FEATURE:
<223> OTHER INFORMATION: nucleic acid element

<400> SEQUENCE: 100
gggtgggagg ggcgggcccc tcccgctttt tttttttgc ggg        43

<210> SEQ ID NO 101
<211> LENGTH: 41
<212> TYPE: DNA
<213> ORGANISM: Artificial Sequence
<220> FEATURE:
<223> OTHER INFORMATION: nucleic acid element

<400> SEQUENCE: 101
gggtgggagg ggcgggccgc cccgcttttt tttttttgcg g         41

<210> SEQ ID NO 102
<211> LENGTH: 42
<212> TYPE: DNA
<213> ORGANISM: Artificial Sequence
<220> FEATURE:
<223> OTHER INFORMATION: nucleic acid element

<400> SEQUENCE: 102
gggtgggagg gtcgggcccg accgcttttt tttttttgcg gt        42

<210> SEQ ID NO 103
<211> LENGTH: 38
<212> TYPE: DNA
<213> ORGANISM: Artificial Sequence
<220> FEATURE:
<223> OTHER INFORMATION: nucleic acid element

<400> SEQUENCE: 103
gggtgggagg ggcgggccac cgcttttttt ttttgcg              38

<210> SEQ ID NO 104
<211> LENGTH: 39
<212> TYPE: DNA
<213> ORGANISM: Artificial Sequence
<220> FEATURE:
<223> OTHER INFORMATION: nucleic acid element

<400> SEQUENCE: 104
gggtgggagg ggcgggccac cccgtttttt tttttcgg             39

<210> SEQ ID NO 105
<211> LENGTH: 40
<212> TYPE: DNA
<213> ORGANISM: Artificial Sequence
<220> FEATURE:
<223> OTHER INFORMATION: nucleic acid element

<400> SEQUENCE: 105

```
gggtgggagg ggcgggtccc acgcttttt ttttttgcgt                              40
```

<210> SEQ ID NO 106
<211> LENGTH: 42
<212> TYPE: DNA
<213> ORGANISM: Artificial Sequence
<220> FEATURE:
<223> OTHER INFORMATION: nucleic acid element

<400> SEQUENCE: 106

```
gggtgggagg ggcgggcccg ccccgctttt tttttttgc gg                           42
```

<210> SEQ ID NO 107
<211> LENGTH: 39
<212> TYPE: DNA
<213> ORGANISM: Artificial Sequence
<220> FEATURE:
<223> OTHER INFORMATION: nucleic acid element

<400> SEQUENCE: 107

```
gggtgggagg ggcgggccac ccgctttttt tttttgcg                               39
```

<210> SEQ ID NO 108
<211> LENGTH: 39
<212> TYPE: DNA
<213> ORGANISM: Artificial Sequence
<220> FEATURE:
<223> OTHER INFORMATION: nucleic acid element

<400> SEQUENCE: 108

```
gggtgggagg ggcgggccct cccgttttt tttttcgg                                39
```

<210> SEQ ID NO 109
<211> LENGTH: 39
<212> TYPE: DNA
<213> ORGANISM: Artificial Sequence
<220> FEATURE:
<223> OTHER INFORMATION: nucleic acid element

<400> SEQUENCE: 109

```
gggtgggagg ggcgggccct ccgtttttt tttttcgga                               39
```

<210> SEQ ID NO 110
<211> LENGTH: 18
<212> TYPE: DNA
<213> ORGANISM: Artificial Sequence
<220> FEATURE:
<223> OTHER INFORMATION: DNAzyme

<400> SEQUENCE: 110

```
ctgggaggga gggaggga                                                     18
```

<210> SEQ ID NO 111
<211> LENGTH: 22
<212> TYPE: DNA
<213> ORGANISM: Artificial Sequence
<220> FEATURE:
<223> OTHER INFORMATION: DNAzyme

<400> SEQUENCE: 111

```
tgagggtggg gagggtgggg aa                                                22
```

<210> SEQ ID NO 112
<211> LENGTH: 18
<212> TYPE: DNA

```
<213> ORGANISM: Artificial Sequence
<220> FEATURE:
<223> OTHER INFORMATION: DNAzyme

<400> SEQUENCE: 112
gtgggtaggg cgggttgg                                                   18

<210> SEQ ID NO 113
<211> LENGTH: 18
<212> TYPE: DNA
<213> ORGANISM: Artificial Sequence
<220> FEATURE:
<223> OTHER INFORMATION: DNAzyme

<400> SEQUENCE: 113
gggcgggccg ggggcggg                                                   18

<210> SEQ ID NO 114
<211> LENGTH: 23
<212> TYPE: DNA
<213> ORGANISM: Artificial Sequence
<220> FEATURE:
<223> OTHER INFORMATION: DNAzyme

<400> SEQUENCE: 114
ggggttgggg tgtgggttg ggg                                              23

<210> SEQ ID NO 115
<211> LENGTH: 16
<212> TYPE: DNA
<213> ORGANISM: Artificial Sequence
<220> FEATURE:
<223> OTHER INFORMATION: DNAzyme

<400> SEQUENCE: 115
gggtgggagg gtcggg                                                     16

<210> SEQ ID NO 116
<211> LENGTH: 18
<212> TYPE: DNA
<213> ORGANISM: Artificial Sequence
<220> FEATURE:
<223> OTHER INFORMATION: aptamer

<400> SEQUENCE: 116
cgcttttttt tttttgcg                                                   18

<210> SEQ ID NO 117
<211> LENGTH: 42
<212> TYPE: DNA
<213> ORGANISM: Artificial Sequence
<220> FEATURE:
<223> OTHER INFORMATION: DNAzyme

<400> SEQUENCE: 117
tgggtgggag ggtcgggccc tcccgctttt ttttttttgc gg                        42

<210> SEQ ID NO 118
<211> LENGTH: 16
<212> TYPE: DNA
<213> ORGANISM: Artificial Sequence
```

```
<220> FEATURE:
<223> OTHER INFORMATION: DNA sensor

<400> SEQUENCE: 118
cccaccctcc cagccc                                                      16
```